United States Patent
Jose

(10) Patent No.: US 8,690,752 B2
(45) Date of Patent: Apr. 8, 2014

(54) OOCYTE SEPARATION AND COLLECTION SYSTEM

(76) Inventor: Alison Jane Jose, McLean, VA (US)

(*) Notice: Subject to any disclaimer, the term of this patent is extended or adjusted under 35 U.S.C. 154(b) by 53 days.

(21) Appl. No.: 13/566,979

(22) Filed: Aug. 3, 2012

(65) Prior Publication Data

US 2014/0038283 A1     Feb. 6, 2014

(51) Int. Cl.
     *A61B 17/43*     (2006.01)
     *A61D 7/00*      (2006.01)

(52) U.S. Cl.
     USPC .............. 600/33; 600/34; 600/35; 604/96.01; 604/890.1; 604/906; 424/561; 128/830; 128/897; 128/898; 128/899

(58) Field of Classification Search
     USPC ............... 600/33–35; 604/96, 890.1; 424/561
     See application file for complete search history.

(56) References Cited

U.S. PATENT DOCUMENTS

| | | | |
|---|---|---|---|
| 3,647,632 A | 3/1972 | Johnson et al. | |
| 4,178,209 A | 12/1979 | Tolbert et al. | |
| 4,639,422 A | 1/1987 | Geimer et al. | |
| 4,731,052 A * | 3/1988 | Seitz, Jr. | 604/540 |
| 4,781,706 A * | 11/1988 | Suzuki et al. | 600/34 |
| 4,824,434 A * | 4/1989 | Seitz, Jr. | 604/27 |
| 5,042,979 A | 8/1991 | Anderson et al. | |
| 5,505,716 A * | 4/1996 | Simmet et al. | 604/318 |
| 5,514,119 A * | 5/1996 | Curtis | 604/319 |
| 6,296,764 B1 | 10/2001 | Guirguis et al. | |
| 2003/0092170 A1 | 5/2003 | Pressman et al. | |
| 2004/0261799 A1 * | 12/2004 | Mock | 128/833 |

* cited by examiner

*Primary Examiner* — Christine Matthews
*Assistant Examiner* — Sunita Reddy
(74) *Attorney, Agent, or Firm* — Ash Tankha; Lipton, Weinberger & Husick

(57) ABSTRACT

An apparatus for separating and collecting one or more oocytes from a fluid mixture includes a chamber inserted into a hollow elongate tube. An inlet channel receives an injected fluid mixture of oocytes and extraneous fluids and passes the fluid mixture to the hollow elongate tube. A separation unit positioned within the chamber includes a porous filter that selectively filters the fluid mixture to retain the oocytes in the hollow elongate tube, and a propeller for agitating the extraneous fluids for allowing unobstructed passage of the extraneous fluids into an outlet channel and for compactly collecting fibrin elements from the extraneous fluids. A flow of the extraneous fluids rotates the propeller on application of a vacuum suction force. Furthermore, the chamber includes an outlet channel for allowing passage of the extraneous fluids separated from the fluid mixture out of the chamber, and retaining the oocytes in the hollow elongate tube.

26 Claims, 11 Drawing Sheets

OOCYTE SEPARATION AND COLLECTION SYSTEM

BACKGROUND

With the advent of artificial reproductive technologies such as in-vitro fertilization which involves follicular aspiration, cryo-preservation, etc., there is a need for precisely extracting oocytes by separating the oocytes from body fluids such as blood, follicular fluid, etc. Follicular aspiration is a procedure that extracts oocytes from the follicles, for example, by puncturing the follicles in a human ovary with a needle which is introduced through the vagina and guided inside the follicles using ultrasound vision. An oocyte is a female gametocyte or a germ cell involved in reproduction. That is, the oocyte is an immature ovum, or an egg cell.

Primary oocytes are present in a human ovary at birth; thereafter, a human female does not form any more oocytes throughout her lifetime. Once a woman reaches sexual maturity, the woman typically starts to ovulate a single oocyte each cycle. The oocytes contained within the ovary are surrounded by a tightly packed corona and granulosa cells. The granulosa cells are also referred to as cumulus cells. The oocyte, the corona, and the granulosa cells are typically referred to as a cumulus complex. One or more oocytes start to mature each month. This results in a development of a fluid filled sac called a follicle around the oocyte and the granulosa or the cumulus complex. As the oocyte matures, the cells become more loosely packed and the size of the follicle increases around the oocyte, until eventually the follicle ruptures. The rupture of the follicle and subsequent release of the oocyte and other follicular contents is referred to as ovulation.

A practical application of culturing of oocytes is in-vitro fertilization. The process of in-vitro fertilization (IVF) requires that the oocytes be collected prior to the occurrence of ovulation. An aspiration needle is used to penetrate each follicle in the ovary using, for example, ultrasound guidance or laparoscopy. The contents of each follicle comprising follicular fluid, oocytes surrounded by corona cells and granulosa cells, detached granulosa cells and corona cells, blood comprising a mixture of red blood cells, white blood cells, plasma, etc., are aspirated into a test tube. As the aspirated fluid mixture passes into the test tube, the fluid mixture is observed, usually by a medical assistant such as a nurse, who informs a medical practitioner to stop the process of aspiration once the level of the fluid mixture approaches an outlet tube. A stopper initially inserted in the test tube is then removed from the test tube and inserted into a fresh test tube into which the next batch of follicular contents is to be transferred. The medical practitioner can then flush or rinse out the collapsed follicle with a flushing fluid which is also aspirated into a test tube. The medical practitioner may then aspirate and flush any other follicles which may be present using the flushing fluid. The flushing fluid is a fluid used for irrigating or rinsing out the collapsed follicles after the contents of the follicles are extracted, or for cleansing the contents in the test tube, by a rapid flow of the fluid. The flushing fluid is, for example, a saline solution, culture media, or other solutions of various salts designed to closely match the fluid found within human fallopian tubes. Each time the fluid level of the fluid mixture in the test tube approaches the outlet tube, the medical practitioner must pause to allow the medical assistant to change the test tube. The filled test tubes are then passed to an embryologist who transfers the contents into a Petri dish and thereafter attempts to locate and isolate any oocytes from the transferred fluid mixture.

Some medical practitioners prefer to keep the contents of each follicle, that is, the oocytes, follicular fluid, oocytes surrounded by corona cells and granulosa cells, detached granulosa cells and corona cells, blood comprising a mixture of red blood cells, white blood cells, plasma, etc., separate while other medical practitioners prefer to group the contents together. The medical practitioner may continue to aspirate follicles until there are no more follicles above a certain size remaining to aspirate. The aspiration process is slowed by having to transfer the stopper into a fresh test tube as the test tube fills up before passing the test tube to an embryologist. This may need constant supervision from a medical assistant who needs to continually monitor the rise of the fluid level in the test tube and to inform the medical practitioner to stop aspirating to allow the stopper to be removed and then inserted into the next fresh test tube. This process may need to be performed several times for each follicle.

Conventional methods and apparatuses for oocyte separation and collection often require that the oocytes be meticulously extracted by skilled clinical technicians using macroscopic and microscopic examination of a combined mixture of fluids comprising, for example, blood fluid, follicular fluid, flushing fluid, etc. Furthermore, the examination and subsequent extraction of oocytes using conventional methods of oocyte separation and collection is often difficult since the waste fluids often comprise blood, which is prone to clotting. Therefore, these methods are also often time consuming and increase the complexity of isolation of oocytes.

Furthermore, conventional methods of oocyte separation and collection often expose the oocytes to temperature variations that may expose the oocytes to thermal stress. When oocytes are collected by a conventional method, the oocytes move from the environment of the human body at approximately 37 Celsius to a room temperature environment of approximately 20 Celsius which is a considerable drop in the surrounding ambient temperature. While suitable efforts are made during the isolation process to maintain the oocytes in their original environmental conditions, that is, according to the environment of the human reproductive system, when the oocytes pass through a fine tubing of an aspiration assembly, the oocytes are not heated and not maintained at a temperature of the environment of the human reproductive system. A test tube that collects the oocytes is typically positioned in a heated test tube rack where the test tube is surrounded by heat conducing material from all sides except the top. However, when the fluid mixture containing the oocytes is poured into a Petri dish for identification and separation of the oocytes from the fluid mixture in the conventional method, there may be a drop in temperature and also exposure to air. The Petri dish is usually examined on a heated microscope stage but the heat only comes, for example, from a base heating element positioned below the Petri dish. These temperature variations induced in the conventional isolation method may expose the oocytes to thermal stress which may interfere with the viability of maintaining the oocytes in a culturing system.

Moreover, conventional methods are often vulnerable to the risk of clotting of the fluids due to exposure of the blood in the fluids to air while aspirating a follicle. Furthermore, in conventional methods for separation and collection of oocytes, oocytes need to be meticulously extracted from a combined mixture of oocytes and associated waste fluids from a Petri dish. However, there is a possibility that the oocytes could be damaged due to variations in the temperature of the Petri dish, changes in potential hydrogen (pH) levels, osmolarity, etc., while transferring the oocytes to the Petri dish or from the Petri dish, etc.

Furthermore, the fluids extracted from the follicle and the flushing fluid for cleaning the oocytes are often injected through an inlet tube that directs the extracted fluids and the flushing fluid into a test tube in a free fall motion which allows the formation of air bubbles within a conventional oocyte collection apparatus. The formation of air bubbles, for example, may obscure the macroscopic and microscopic visualization of the oocytes. Furthermore, the oocytes may be exposed to mechanical stress as a result of the free fall motion of the fluids containing the oocytes and the flushing fluid, in the conventional oocyte collection apparatus, potentially damaging the oocytes.

The oocytes are generally collected sequentially, one at a time unless a medical practitioner penetrates two or more follicles simultaneously. The contents from each follicle may be divided between two or more test tubes, each of which must be meticulously searched by an embryologist for oocytes. There is a need for an apparatus that collects only the desirable contents of a follicle or more than one follicle in a single test tube and passes the test tube to the embryologist for considerably speeding up the work of the embryologist and hence the entire procedure.

Hence, there is a long felt but unresolved need for an apparatus and a method that quickly performs separation and collection of a single oocyte or multiple oocytes at a time by filtering a fluid mixture comprising one or more oocytes and extraneous fluids, while minimizing exposure of the oocytes to thermal stress and mechanical stress, without causing damage to the oocytes, thereby collecting oocytes that are more easily contained, harvested, and available for storage and use. Furthermore, there is a need for an apparatus and a method that enables transfer of only the extraneous fluids of the fluid mixture out of an oocyte receptacle, thereby allowing retention and collection of only the oocytes in a minimal volume of the fluid mixture in the oocyte receptacle. Furthermore, there is a need for an apparatus and a method that enables medical practitioners to contain the oocytes and therefore preclude the risk of inadvertently discarding the oocytes.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

The apparatus and method disclosed herein address the above stated needs for quickly separating and collecting a single oocyte or multiple oocytes at a time by filtering a fluid mixture which contains one or more oocytes and extraneous fluids, while minimizing exposure of the oocytes to thermal stress and mechanical stress, without causing damage to the oocytes, thereby collecting oocytes that are more easily contained, harvested, and available for storage and use. As used herein, the term "fluid mixture" refers to a mixture of fluids comprising, for example, contents including one or more oocytes extracted from one or more follicles and fluids introduced into a hollow elongate tube, that is, a test tube during follicular aspiration such as a flushing fluid used for cleaning the oocytes. The contents extracted from one or more follicles comprise, for example, one or more oocytes, follicular fluid, corona cells and granulosa cells surrounding the oocytes, detached granulosa cells and corona cells, blood comprising a mixture of red blood cells, white blood cells, plasma, etc. Also, as used herein, the term "extraneous fluids" refers to fluids and other particulates external to the oocytes. For example, the extraneous fluids comprise the follicular fluid, the corona cells and the granulosa cells surrounding the oocytes, the detached granulosa cells and corona cells, blood comprising a mixture of red blood cells, white blood cells, plasma, flushing fluid used for cleaning the oocytes, etc. The flushing fluid is a fluid used for irrigating or rinsing out the follicles after the contents of the follicles are extracted, or for cleansing the contents in the test tube, by a rapid flow of the fluid. The flushing fluid is, for example, a saline solution, culture media, or other solutions of various salts designed to closely match the fluid found within human fallopian tubes. Also, the term "follicular aspiration" refers to a procedure that extracts oocytes from the follicles, for example, by puncturing the follicles in a human ovary with an aspiration needle which is introduced through the vagina and guided inside the follicles using ultrasound vision.

The apparatus and method disclosed herein collects only the desirable contents of a follicle or more than one follicle in a single test tube and passes the test tube to an embryologist, thereby considerably speeding up the work of the embryologist and hence the entire procedure. The apparatus and method disclosed herein also address the above stated need for enabling transfer of only the extraneous fluids of the fluid mixture out of an oocyte receptacle, thereby allowing retention and collection of only the oocytes in a minimal volume of the fluid mixture in the oocyte receptacle. The apparatus and method disclosed herein also address the above stated need for enabling medical practitioners to contain the oocytes and therefore preclude the risk of inadvertently discarding the oocytes.

Furthermore, the apparatus and method disclosed herein enable performance of faster surgical procedures, for example, procedures for follicular aspiration, subsequent cell culture procedures, etc., since the apparatus and method disclosed herein enables quicker separation of the oocytes from the fluid mixture. Furthermore, the apparatus and method disclosed herein require a medical assistant to change a stopper-aspiration device assembly into a fresh test tube only when a medical practitioner wants to start a new grouping of oocytes. That is, the apparatus and method disclosed herein do not require constant supervision by a medical assistant on whether the fluid level of the fluid mixture contained in the test tube has risen in the test tube since, in the apparatus and method disclosed herein, the excess fluid is removed to a waste container.

The configuration of the apparatus disclosed herein facilitates reduction in the formation of air bubbles in the fluid mixture within the test tube, facilitates reduction in the agitation of the fluid mixture caused by the drop of the fluid mixture to a closed lower end of the test tube, and precludes or reduces exposure of the oocytes to temperature variations that may expose the oocytes to thermal stress which may interfere with the viability of maintaining the oocytes in a culturing system.

The apparatus for separating and collecting one or more oocytes from a fluid mixture disclosed herein comprises a chamber configured for insertion into a hollow elongate tube. The chamber is configured, for example, as a generally cylindrical chamber, a rectangular chamber, etc. The chamber comprises an upper end and a lower end. The hollow elongate tube has an open upper end and a closed lower end. The chamber is in gripping contact with an inner wall surface of the hollow elongate tube. In an embodiment, the apparatus disclosed herein comprises a sealing element configured to provide the gripping contact between the chamber and the inner wall surface of the hollow elongate tube.

The chamber comprises an inlet channel, a separation unit, and an outlet channel. The inlet channel extends within the chamber from the upper end of the chamber to the lower end of the chamber. The inlet channel is configured to receive an inlet tube of an aspiration assembly that injects the fluid mixture comprising one or more oocytes and extraneous fluids into the inlet channel towards the closed lower end of the hollow elongate tube. In an embodiment, the inlet channel receives the inlet tube of the aspiration assembly via a first longitudinal opening of a stopper positioned in a fluid tight configuration at the upper end of the chamber, for receiving the fluid mixture from the aspiration assembly via the inlet tube. The inlet channel is in fluid communication with a receiving section bounded by the closed lower end of the hollow elongate tube and the lower end of the chamber, via an opening defined at the lower end of the chamber, for allowing passage of the fluid mixture from within the inlet channel towards the closed lower end of the hollow elongate tube. The fluid mixture maintains contact with the inner sides of the inlet channel during passage of the fluid mixture through the inlet channel. The receiving section receives the fluid mixture from the inlet channel via the opening defined at the lower end of the chamber. The separation unit is positioned within the chamber at the lower end of the chamber. The separation unit comprises one or more walls and a ceiling. The separation unit further comprises a porous filter rigidly positioned within a cavity defined at the lower end of the chamber. The porous filter is configured to selectively filter the fluid mixture to retain the oocytes from the fluid mixture at the closed lower end of the hollow elongate tube. The porous filter comprises multiple pores for selectively filtering the fluid mixture to retain the oocytes at the closed lower end of the hollow elongate tube. The diameter of each of the pores of the porous filter is less than a diameter of each of the oocytes and is configured to allow the flow of a substantial portion of the extraneous fluids through the pores of the porous filter into the outlet channel.

In an embodiment, the separation unit further comprises a propeller rigidly suspended from the ceiling of the separation unit within a space defined by the porous filter, the walls, and the ceiling of the separation unit. The propeller is rotated by a flow of a substantial portion of the extraneous fluids into the defined space via the porous filter, on an application of a vacuum suction force from a vacuum suction element operably coupled to an outlet tube of the aspiration assembly via a waste collection container. The rotation of the propeller agitates a substantial portion of the extraneous fluids for allowing unobstructed passage of a substantial portion of the extraneous fluids into the outlet channel via an opening in the ceiling of the separation unit.

When an oocyte is drawn from an ovary, blood may also be drawn out due to rupturing of blood vessels around an ovarian follicle containing the oocyte. The blood fluid comprises fibrin elements that are responsible for blood coagulation. The rotation of the propeller enables compact collection of the fibrin elements from the extraneous fluids on the propeller to preclude clotting and allow the unobstructed passage of a substantial portion of the extraneous fluids into the outlet channel. The separation unit therefore compactly collects the fibrin elements from the extraneous fluids separated from the fluid mixture as they form.

The outlet channel extends longitudinally from the opening in the ceiling of the separation unit to the upper end of the chamber. The outlet channel is in fluid communication with the space defined by the porous filter, one or more walls, and the ceiling of the separation unit via the opening in the ceiling for allowing passage of a substantial portion of the extraneous fluids separated from the fluid mixture out of the chamber. The outlet channel is configured to receive the outlet tube of the aspiration assembly for allowing a substantial portion of the extraneous fluids separated from the fluid mixture to be withdrawn out of the chamber, on the application of the vacuum suction force, and for allowing the oocytes to be retained and collected at the closed lower end of the hollow elongate tube.

The outlet channel receives the outlet tube of the aspiration assembly via a second longitudinal opening of the stopper positioned in a fluid tight configuration at the upper end of the chamber for allowing the substantial portion of the extraneous fluids to be withdrawn from the space defined by the porous filter, one or more walls, and the ceiling of the separation unit. In an embodiment, the outlet channel allows a substantial portion of the extraneous fluids to be withdrawn from the defined space via the outlet tube on the application of vacuum suction force. The receiving section bounded by the closed lower end of the hollow elongate tube and the lower end of the chamber retains and collects the oocytes after a substantial portion of the extraneous fluids separated from the fluid mixture is withdrawn out of the chamber via the outlet channel.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and components disclosed herein.

DETAILED DESCRIPTION OF THE INVENTION

Figure 1A:
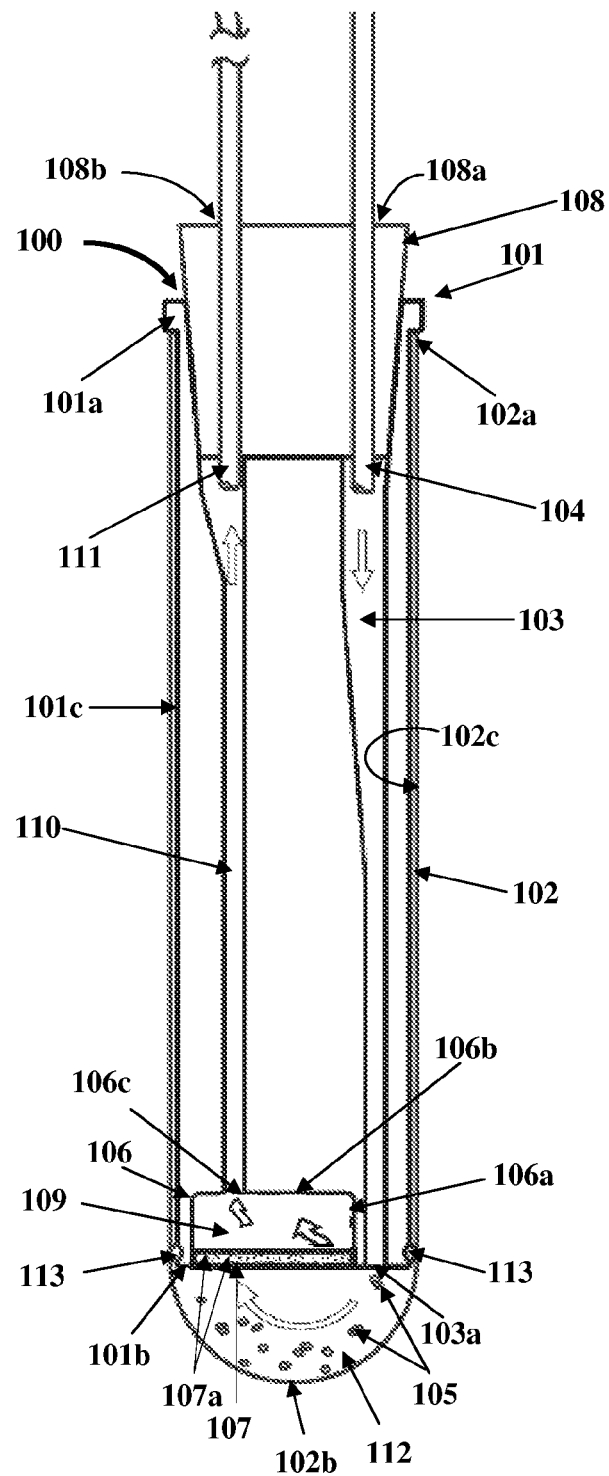
FIG. 1A exemplarily illustrates a front elevation view of an oocyte separation apparatus inserted into a hollow elongate tube for separating and collecting one or more oocytes from a fluid mixture.

FIG. 1A exemplarily illustrates a front elevation view of an oocyte separation apparatus 100 inserted into a hollow elongate tube 102 for separating and collecting one or more oocytes 105 from a fluid mixture which contains one or more oocytes 105 and extraneous fluids. As used herein, the term "fluid mixture" refers to a mixture of fluids comprising, for example, contents including one or more oocytes 105 extracted from one or more follicles and fluids introduced into the hollow elongate tube 102 during follicular aspiration such as flushing fluid used for cleaning the oocytes 105. The contents extracted from one or more follicles comprise, for example, one or more oocytes 105, follicular fluid, corona cells and granulosa cells surrounding the oocytes 105, detached granulosa cells and corona cells, blood comprising a mixture of red blood cells, white blood cells, plasma, etc. The follicular fluid is a liquid that surrounds the ovum in a follicle, where a follicle is a basic unit of human reproductive biology, found in the ovary, composed of an aggregation of cells. The cells of the follicle comprise the oocyte 105, granulosa cells, and the cells of the internal and external theca layers. Also, as used herein, the term "extraneous fluids" refers to fluids and other particulates external to the oocytes 105. For example, the extraneous fluids comprise the follicular fluid, the corona cells and the granulosa cells surrounding the oocytes 105, the detached granulosa cells and corona cells, blood comprising a mixture of red blood cells, white blood cells, plasma, flushing fluid used for cleaning the oocytes 105, etc. The flushing fluid is a fluid used for irrigating or rinsing out the follicles after the contents of the follicles are extracted, or for cleansing the contents in the hollow elongate tube 102, by a rapid flow of the fluid. The flushing fluid is, for example, a saline solution, culture media, or other solutions of various salts designed to closely match the fluid found within human fallopian tubes.

The oocyte separation apparatus 100 disclosed herein comprises a chamber 101 configured for insertion into a hollow elongate tube 102, for example, a test tube. The chamber 101 is configured, for example, as a generally cylindrical chamber 101, a cuboidal chamber, etc. For purposes of illustration, the detailed description refers to a generally cylindrical chamber 101 as exemplarily illustrated in FIGS. 1A-8; however the scope of the oocyte separation apparatus 100 disclosed herein is not limited to the generally cylindrical chamber 101 but may be extended to include a chamber 101 of different functionally equivalent shapes. The chamber 101 is configured to be sterilizable to be maintained in a sterile state and to be disposable after a single use. The chamber 101 is individually packaged and sterilized, for example, by gamma beam irradiation or an electron beam (e-beam) irradiation and handled using aseptic techniques during oocyte separation and collection. The chamber 101 comprises an upper end 101a and a lower end 101b. The hollow elongate tube 102 has an open upper end 102a and a closed lower end 102b.

In an embodiment, the chamber 101 is in gripping contact with an inner wall surface 102c of the hollow elongate tube 102. In another embodiment, the oocyte separation apparatus 100 disclosed herein comprises a sealing element 113 configured to provide a gripping contact between the chamber 101 and the inner wall surface 102c of the hollow elongate tube 102. The sealing element 113 is, for example, an O-ring seal. An O-ring, also known as a packing joint or a toric joint, is a mechanical gasket in the shape of a torus. The O-ring is a loop of elastomer with a disc shaped cross section, configured to be seated in a groove 101d positioned proximal to the lower end 101b of the chamber 101 as exemplarily illustrated in FIG. 2, and configured to be compressed during insertion of the chamber 101 into the hollow elongate tube 102, thereby creating a seal at the interface between the outer surface 101c of the chamber 101 and the inner wall surface 102c of the hollow elongate tube 102.

The chamber 101 comprises an inlet channel 103, a separation unit 106, and an outlet channel 110. The inlet channel 103 is configured to receive an inlet tube 104 of an aspiration assembly 501 exemplarily illustrated in FIG. 5. The inlet tube 104 feeds the fluid mixture comprising the oocytes 105 and the extraneous fluids into the inlet channel 103 and towards the closed lower end 102b of the hollow elongate tube 102 through an opening 103a defined at the lower end 101b of the chamber 101. In an embodiment, the inlet channel 103 receives the inlet tube 104 of the aspiration assembly 501 via a first longitudinal opening 108a of a stopper 108 positioned in a fluid tight configuration at the upper end 101a of the chamber 101, for receiving the fluid mixture from the aspiration assembly 501 via the inlet tube 104 as disclosed in the detailed description of FIG. 6. As exemplarily illustrated in FIGS. 1A-1B, the stopper 108 is shown inserted into the chamber 101 of the oocyte separation apparatus 100. The stopper 108, for example, a silicone bung that is a part of the aspiration assembly 501, positions the inlet tube 104 and an outlet tube 111 in the oocyte separation apparatus 100. The inlet channel 103 allows passage of the fluid mixture from within the inlet channel 103 towards the closed lower end 102b of the hollow elongate tube 102 via the opening 103a of the inlet channel 103.

The separation unit 106 is positioned within the chamber 101 at the lower end 101b of the chamber 101. The separation unit 106 comprising one or more walls 106a, for example, a generally cylindrical wall 106a, a ceiling 106b, and a porous filter 107 is disclosed in the detailed description of FIG. 2. The porous filter 107 of the separation unit 106 is configured to selectively filter the fluid mixture to retain one or more oocytes 105 from the fluid mixture at the closed lower end 102b of the hollow elongate tube 102. The outlet channel 110 is configured to receive an outlet tube 111 of the aspiration assembly 501, exemplarily illustrated in FIG. 5, for allowing a substantial portion of the extraneous fluids separated from the fluid mixture to be withdrawn out of the chamber 101, on an application of the vacuum suction force as disclosed in the detailed description of FIG. 6.

In an embodiment, the outlet channel 110 is in fluid communication with the outlet tube 111 of the aspiration assembly 501. The outlet tube 111 exits the chamber 101 via a second longitudinal opening 108b of the stopper 108 positioned in a fluid tight configuration at the upper end 101a of the chamber 101, for allowing a substantial portion of the extraneous fluids to be withdrawn from a space 109 defined by the porous filter 107, the generally cylindrical wall 106a, and the ceiling 106b of the separation unit 106. The outlet tube 111 receives a substantial portion of the extraneous fluids from the outlet channel 110 and allows passage of the substantial portion of the extraneous fluids out of the chamber 101 into a waste collection container 508 exemplarily illustrated in FIG. 5.

Figure 1B:
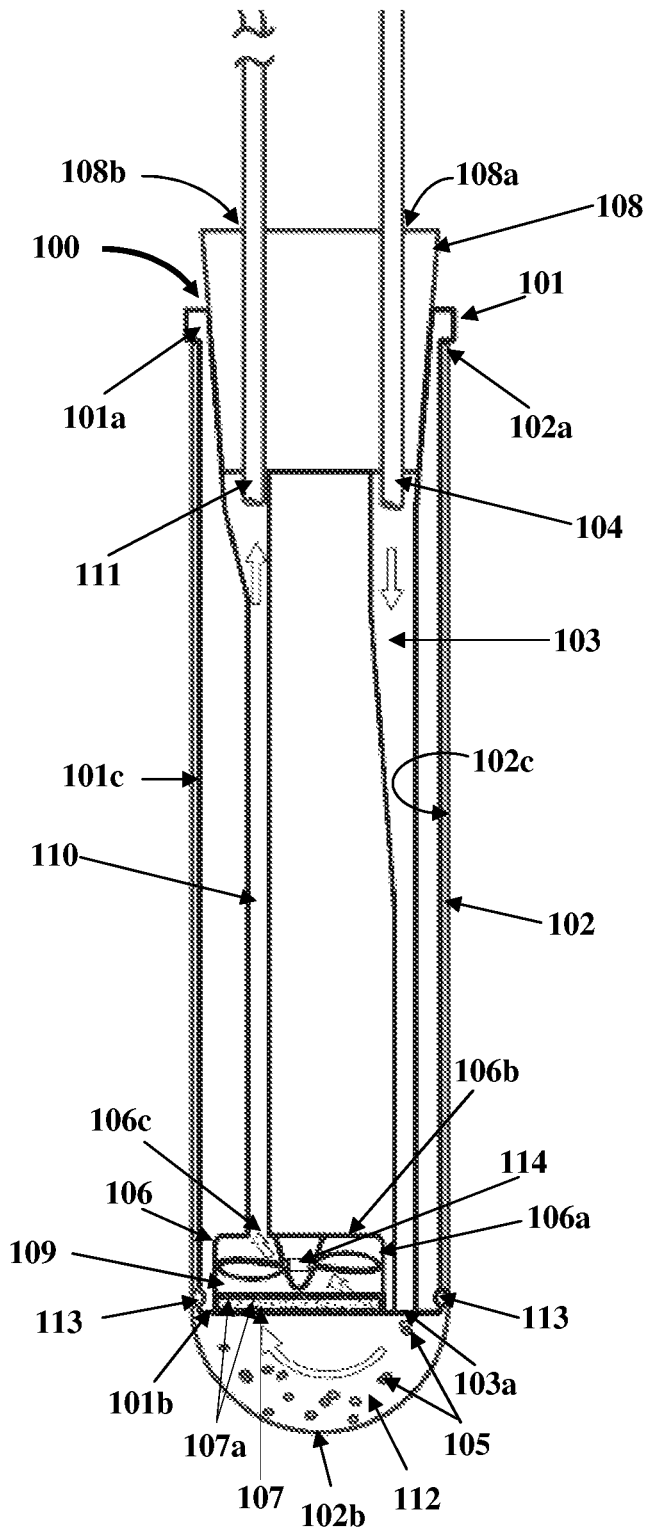
FIG. 1B exemplarily illustrates a front elevation view of an embodiment of the oocyte separation apparatus inserted into a hollow elongate tube for separating and collecting one or more oocytes from a fluid mixture, where the oocyte separation apparatus comprises a propeller.

FIG. 1B exemplarily illustrates a front elevation view of an embodiment of the oocyte separation apparatus 100 inserted into a hollow elongate tube 102 for separating and collecting one or more oocytes 105 from a fluid mixture, where the oocyte separation apparatus 100 comprises a propeller 114. The oocyte separation apparatus 100 comprises the chamber 101, the inlet channel 103, the separation unit 106, and the outlet channel 110 as disclosed in the detailed description of FIG. 1A. Furthermore, in this embodiment, the separation unit 106 further comprises the propeller 114. The structural details of the propeller 114 are disclosed in the detailed description of FIG. 2. Rotation of the propeller 114 of the separation unit 106 enables compact collection of fibrin elements from the extraneous fluids on the propeller 114 to preclude clotting for unobstructed passage of a substantial portion of the extraneous fluids into the outlet channel 110 as disclosed in the detailed description of FIG. 6 and FIG. 8. The term "fibrin" used herein, refers to a fibrous, non-globular, insoluble protein involved in the clotting of blood. The fibrin protein is formed from a soluble protein fibrinogen that is present in blood plasma, and is then polymerized to form a mesh that forms a hemostatic plug or a clot over a wound site. The wound site may be created at a point of penetration of the follicle by an aspiration needle 502 exemplarily illustrated in FIG. 5. A number of molecules of the fibrin protein combine to form a "fibrin element" or a fibrin thread. The fibrin elements may interfere with the separation of a substantial portion of the extraneous fluids from the oocytes 105 since they form blood clots that obstruct the passage of the substantial portion of the extraneous fluids out of the chamber 101.

Figure 2:
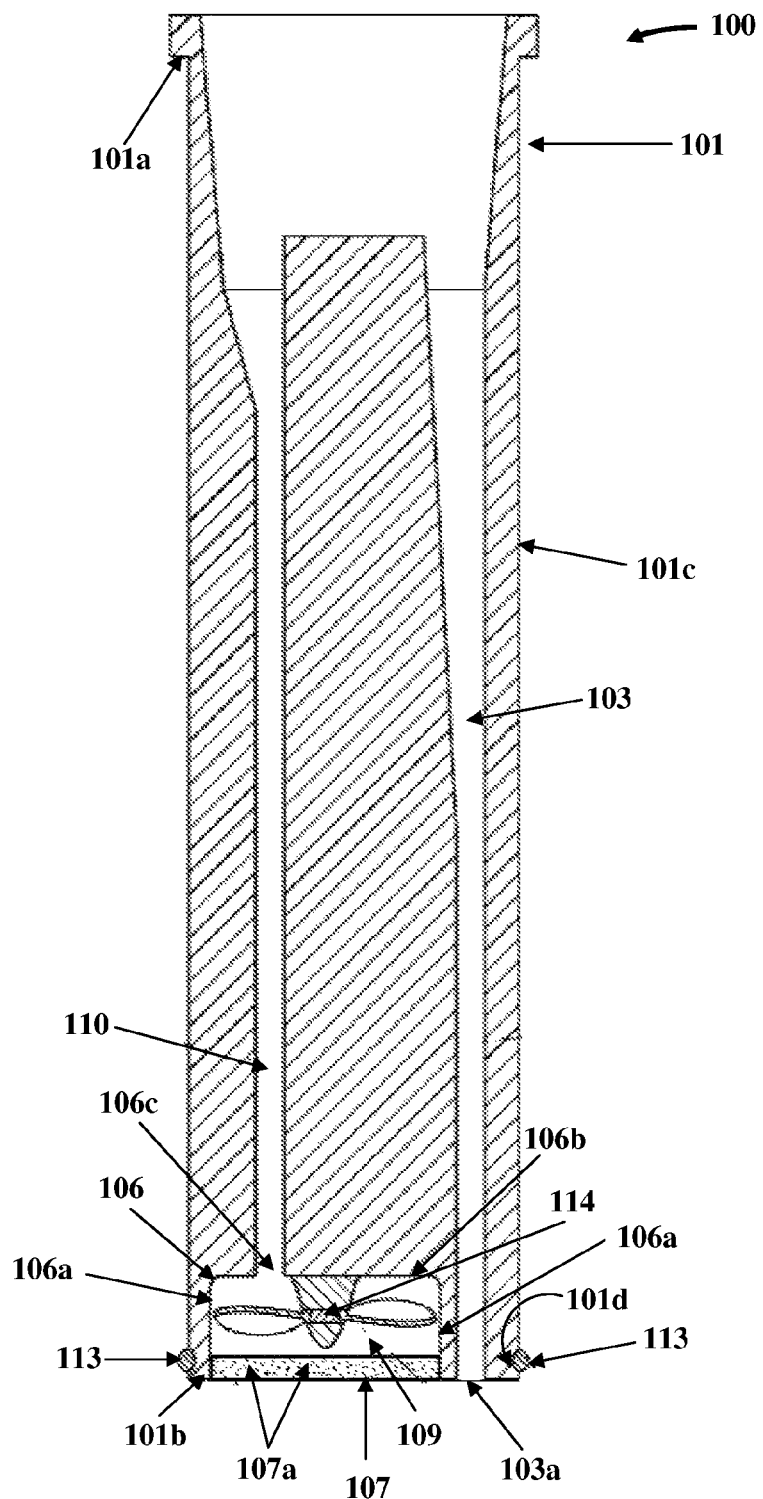
FIG. 2 exemplarily illustrates a sectional view of a chamber of the oocyte separation apparatus for separating one or more oocytes from a fluid mixture.

FIG. 2 exemplarily illustrates a sectional view of the chamber 101 of the oocyte separation apparatus 100 for separating one or more oocytes 105 from a fluid mixture. The chamber 101 comprises an inlet channel 103, a separation unit 106, and an outlet channel 110 as disclosed in the detailed description of FIG. 1A. The inlet channel 103 extends within the chamber 101 from the upper end 101a of the chamber 101 to the lower end 101b of the chamber 101. In an embodiment, the inlet channel 103 partially tapers from the upper end 101a of the chamber 101 to the lower end 101b of the chamber 101. An opening 103a of the inlet channel 103 is defined at the lower end 101b of the chamber 101.

The separation unit 106 is, for example, configured as a cylindrical housing, a cuboidal housing, etc., positioned within the chamber 101 at the lower end 101b of the chamber 101. For purposes of illustration, the detailed description refers to a generally cylindrical separation unit 106; however, the scope of the oocyte separation apparatus 100 disclosed herein is not limited to the generally cylindrical separation unit 106 but may be extended to include a separation unit 106 of different functionally equivalent shapes. The generally cylindrical separation unit 106 comprises a generally cylindrical wall 106a, a ceiling 106b, a porous filter 107, and a propeller 114. The separation unit 106 extends from the porous filter 107 at the lower end 101b of the chamber 101 to the ceiling 106b, within the chamber 101 of the oocyte separation apparatus 100. The porous filter 107, the cylindrical wall 106a, and the ceiling 106b define an enclosed space 109 therebetween for retrieving a substantial portion of the extraneous fluids free from the oocytes 105 from the fluid mixture.

Figure 3:
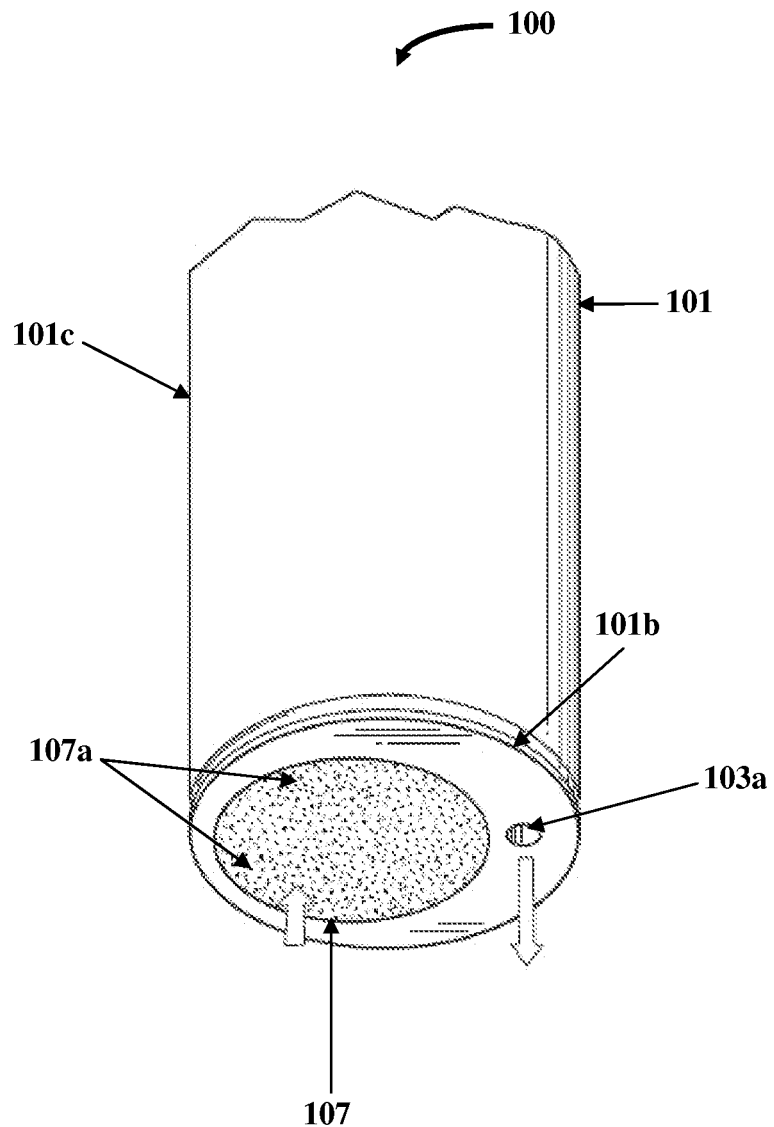
FIG. 3 exemplarily illustrates a partial bottom perspective view of the oocyte separation apparatus.
Figure 4:
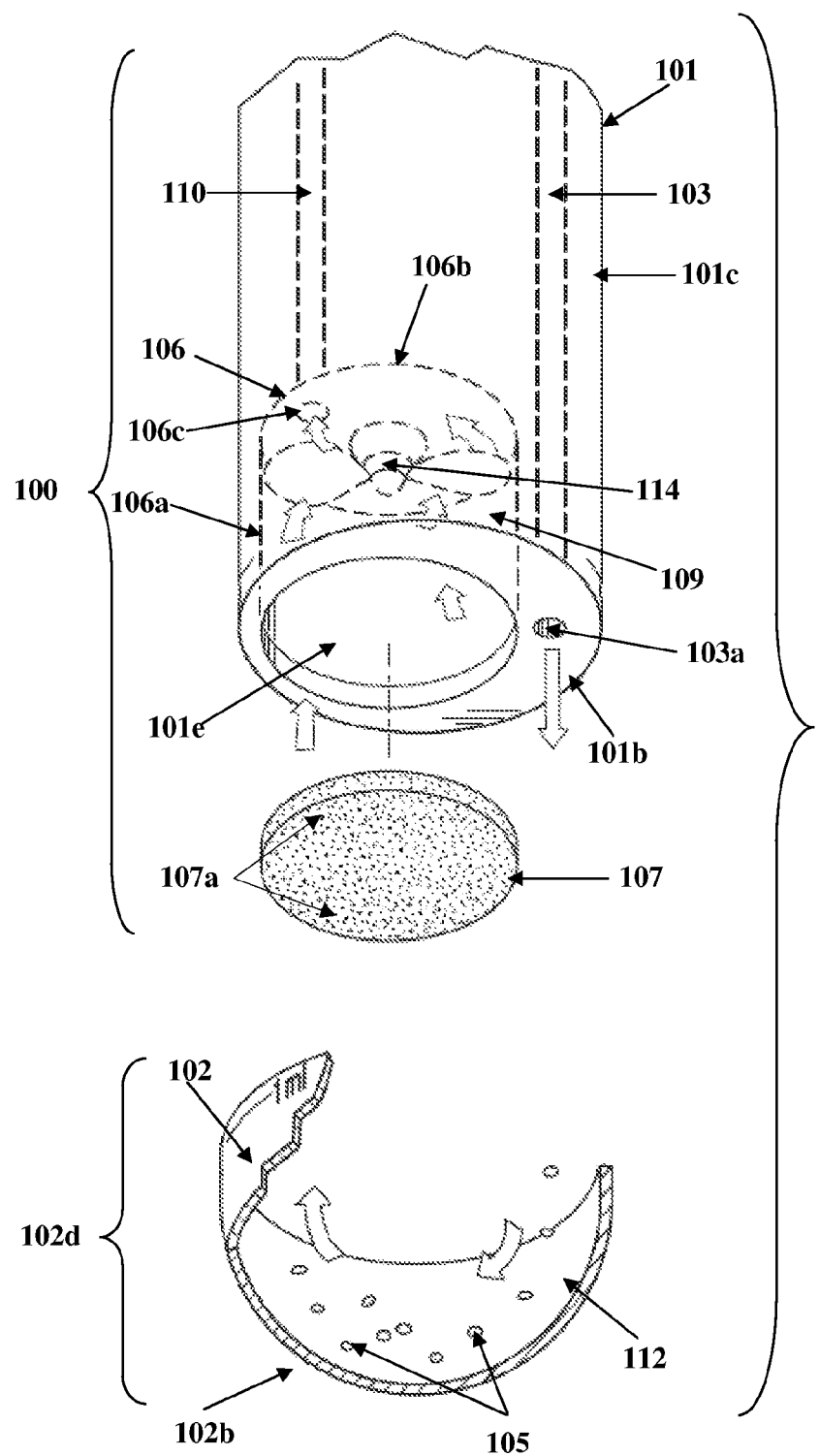
FIG. 4 exemplarily illustrates a partially exploded view of the oocyte separation apparatus in communication with a receiving section bounded by the closed lower end of the hollow elongate tube and the lower end of the chamber of the oocyte separation apparatus.

The porous filter 107 of the separation unit 106 is rigidly positioned within a cavity 101e defined at the lower end 101b of the chamber 101 as exemplarily illustrated in FIGS. 3-4. The porous filter 107 is configured to selectively filter the fluid mixture to retain the oocytes 105 at the closed lower end 102b of the hollow elongate tube 102 as disclosed in the detailed description of FIG. 4. Furthermore, the porous filter 107 allows the passage of a substantial portion of the extraneous fluids and particles that are smaller than oocytes 105, for example, blood cells, into the outlet channel 110 for collection into a waste collection container 508 exemplarily illustrated in FIG. 5. The propeller 114 of the separation unit 106 is rigidly suspended from the ceiling 106b of the separation unit 106 within a space 109 defined by the porous filter 107, the generally cylindrical wall 106a, and the ceiling 106b of the separation unit 106. On an application of a vacuum suction force from a vacuum suction element 507 exemplarily illustrated in FIG. 5, a flow of a substantial portion of the extraneous fluids into the defined space 109 via the porous filter 107 rotates the propeller 114. In an embodiment, the propeller 114 is also rotated by a mini-motor (not shown) powered by a battery (not shown) built into the propeller housing. The rotation of the propeller 114 agitates the substantial portion of the extraneous fluids for allowing unobstructed passage of the substantial portion of the extraneous fluids into an outlet channel 110 via an opening 106c in the ceiling 106b of the separation unit 106.

The outlet channel 110 extends longitudinally from the opening 106c in the ceiling 106b of the separation unit 106 to the upper end 101a of the chamber 101. The outlet channel 110 is in fluid communication with the space 109 defined by the porous filter 107, the generally cylindrical wall 106a, and the ceiling 106b of the separation unit 106 via the opening 106c in the ceiling 106b to allow the passage of the substantial portion of the extraneous fluids separated from the fluid mixture out of the chamber 101.

FIG. 3 exemplarily illustrates a partial bottom perspective view of the oocyte separation apparatus 100. The chamber 101 of the oocyte separation apparatus 100 exemplarily illustrated in FIG. 3 is generally cylindrical in shape. The chamber 101 comprises a cavity 101e exemplarily illustrated in FIG. 4, defined at the lower end 101b of the chamber 101, which enables the porous filter 107 to be rigidly positioned at the lower end 101b of the chamber 101. Furthermore, the chamber 101 comprises an opening 103a defined at the lower end 101b of the chamber 101 that enables the inlet channel 103 to remain in fluid communication with a receiving section 112 of the hollow elongate tube 102 exemplarily illustrated on FIG. 4, for allowing the fluid mixture injected by the aspiration assembly 501 exemplarily illustrated in FIG. 5, to flow to the closed lower end 102b of the hollow elongate tube 102.

FIG. 4 exemplarily illustrate a partially exploded view of the oocyte separation apparatus 100 in communication with a receiving section 112 bounded by the closed lower end 102b of the hollow elongate tube 102 and the lower end 101b of the chamber 101 of the oocyte separation apparatus 100. FIG. 4 exemplarily illustrates the oocyte separation apparatus 100 comprising the chamber 101 of a generally cylindrical shape. FIG. 4 also exemplarily illustrates a bottom perspective view of the oocyte separation apparatus 100, showing the cavity 101e defined at the lower end 101b of the chamber 101 for rigidly positioning the porous filter 107 of the generally cylindrical separation unit 106. FIG. 4 also exemplarily illustrates a bottom portion 102d of the hollow elongate tube 102 that partially defines the receiving section 112 for collecting the oocytes 105 from the fluid mixture. The inlet channel 103 of the oocyte separation apparatus 100 is in fluid communication with the receiving section 112 bounded by the closed lower end 102b of the hollow elongate tube 102 and the lower end 101b of the chamber 101, via the opening 103a defined at the lower end 101b of the chamber 101, for allowing passage of the fluid mixture from within the inlet channel 103 towards the closed lower end 102b of the hollow elongate tube 102. The receiving section 112 of the hollow elongate tube 102 receives the fluid mixture from the inlet channel 103, allows a substantial portion of the extraneous fluids separated from the fluid mixture to be filtered through the porous filter 107 and thereafter withdrawn out of the chamber 101 via the outlet channel 110, and retains and collects the oocytes 105 at the closed lower end 102b of the hollow elongate tube 102. For purposes of illustration, the detailed description refers to separation and collection of multiple oocytes 105 from the fluid mixture, however the scope of the oocyte separation apparatus 100 disclosed herein may also be used for separation and collection of a single oocyte 105 contained in the fluid mixture.

The generally cylindrical separation unit 106 is positioned within the chamber 101 at the lower end 101b of the chamber 101. The separation unit 106 comprises a generally cylindrical wall 106a and a ceiling 106b. The porous filter 107 of the separation unit 106 is rigidly positioned within the cavity 101e defined at the lower end 101b of the chamber 101 as exemplarily illustrated in FIG. 3. The porous filter 107 comprises multiple pores 107a for selective filtration of the fluid mixture to retain the oocytes 105 at the closed lower end 102b of the hollow elongate tube 102. The diameter of each of the pores 107a of the porous filter 107 is lesser than a diameter of each of the oocytes 105 and is configured to allow the flow of a substantial portion of the extraneous fluids through the pores 107a of the porous filter 107. For example, the diameter of the oocytes 105 is about 100 microns to about 120 microns. The diameter of red blood cells is typically between, for example, about 6 microns and about 8 microns, and the diameter of neutrophils is typically between, for example, about 9 microns and about 16 microns. The neutrophils are a type of white blood cells. The red blood cells and the neutrophils are constituent cellular components of blood. It is possible that blood may be drawn out along with the oocytes 105, and without filtering, may collect alongside the oocytes 105 and interfere with the culturing. Since the diameter of each of the pores 107a of the porous filter 107 is greater than the diameter of each of the red blood cells and the neutrophils, the porous filter 107 separates these cellular components from the oocytes 105. The porous filter 107 is, for example, a nylon net filter with a pore size of about 60 microns to about 80 microns. The porous filter 107 is, for example, a Millipore filter of Millipore Corporation or a nucleopore filter in which pores 107a a few micrometers in size are created in a plastic membrane such as a polycarbonate membrane. The porous filter 107 can be configured into discs. The porous filter 107 is sterilizable, for example, by gamma beam irradiation or by using ethylene oxide. The diameter of each of the pores 107a of the porous filter 107 is configured to be lesser than or equal to about 100 microns. Since the size of the pores 107a of the porous filter 107 is smaller than the size of the oocytes 105 but greater than the size of the other particles within the extraneous fluids, the porous filter 107 disallows the passage of the oocytes 105 through the pores 107a of the porous filter 107 and allows the passage of the extraneous fluids along with the particles of the extraneous fluids through the pores 107a, thereby retaining the oocytes 105 and facilitating the collection of the oocytes 105 in the receiving section 112 at the closed lower end 102b of the hollow elongate tube 102. As an oocyte 105 matures within the follicle, the oocyte 105 is surrounded by granulosa cells. Some of the granulosa cells, either as singular granulosa cells or as part of aggregate clumps of granulosa cells, may be detached from the oocyte 105. The size of each of the granulosa cells varies. The aggregate clumps of granulosa cells may, for example, have a dimension greater than the diameter of the pores 107a of the porous filter 107. In this case, the porous filter 107 allows the passage of singular granulosa cells out of the chamber 101 but retains the aggregate clumps of granulosa cells with the oocytes 105. As the oocyte 105 matures, the granulosa cells become less tightly packed and start to disperse.

Figure 5:
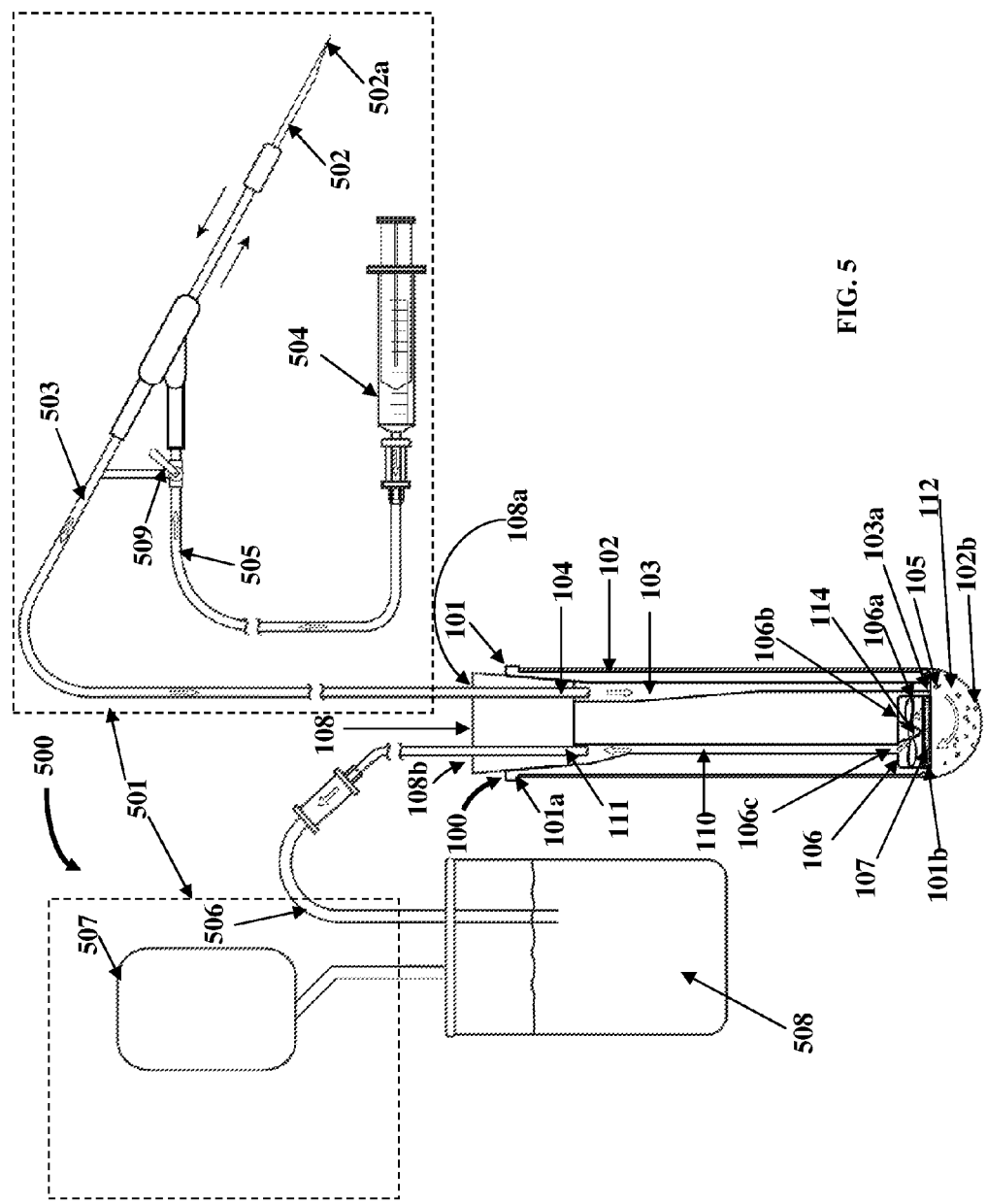
FIG. 5 exemplarily illustrates an oocyte separation and collection system for separating and collecting one or more oocytes from a fluid mixture.

The outlet channel 110 allows a substantial portion of the extraneous fluids from the space 109 defined by the porous filter 107, the cylindrical wall 106a, and the ceiling 106b of the separation unit 106 to be aspirated out of the chamber 101, on the application of the vacuum suction force from the vacuum suction element 507 of the aspiration assembly 501 exemplarily illustrated in FIG. 5, allowing the oocytes 105 to be retained in the receiving section 112 at the closed lower end 102b of the hollow elongate tube 102.

FIG. 5 exemplarily illustrates an oocyte separation and collection system 500 for separating and collecting one or more oocytes 105 from a fluid mixture. The oocyte separation and collection system 500 disclosed herein comprises the oocyte separation apparatus 100 as disclosed in the detailed descriptions of FIGS. 1A-4, the hollow elongate tube 102, an aspiration assembly 501, and a waste collection container 508. The oocyte separation apparatus 100 comprising the chamber 101 is inserted into the hollow elongate tube 102. The stopper 108 is positioned in a fluid tight configuration at the upper end 101a of the chamber 101. The inlet tube 104 and the outlet tube 111 of the aspiration assembly 501 are inserted into the longitudinal openings 108a and 108b of the stopper 108 respectively. As exemplarily illustrated in FIG. 5, the oocyte separation apparatus 100 acts as an interface between the inlet tube 104 and the outlet tube 111 of the aspiration assembly 501. The aspiration assembly 501 aspirates oocytes 105 from an ovary. The aspiration assembly 501 comprises an aspiration needle 502, an aspiration line 503, a syringe 504, a flushing line 505, the inlet tube 104, the outlet tube 111, a vacuum suction line 506, and a vacuum suction element 507. The aspiration assembly 501 is, for example, a sterile single use device which is incorporated with the vacuum suction line 506. The waste collection container 508 is external to the aspiration assembly 501 and used in conjunction with the oocyte separation apparatus 100. The vacuum suction line 506 is inserted into the waste collection container 508.

The aspiration needle 502 of the aspiration assembly 501 extracts contents of the ovarian follicles directly from the ovarian follicles of a patient and transfers the contents to the inlet channel 103 within the chamber 101 via the inlet tube 104. The contents extracted from the ovarian follicles comprise, for example, one or more oocytes 105, follicular fluid, corona cells and granulosa cells surrounding the oocytes 105, detached granulosa cells and corona cells, blood comprising a mixture of red blood cells, white blood cells, plasma, etc. In an example, the aspiration needle 502 is vaginally inserted into the patient using ultrasound guidance such that one end 502a of the aspiration needle 502 is in contact with an ovary of the patient. The aspiration needle 502 punctures an ovarian follicle to extract the oocyte 105 along with the other contents of the ovarian follicle. The syringe 504 of the aspiration assembly 501 injects a flushing fluid through the flushing line 505. The injected flushing fluid passes through the aspiration needle 502 and flushes out any retained oocyte from inside the punctured ovarian follicle. The flushing fluid is drawn out after the contents of the ovarian follicle with or without the oocyte 105 into the aspiration line 503 of the aspiration assembly 501. Since there is only a single oocyte in each follicle, the flushing fluid is used to increase the chances of detaching the oocyte from an interior of the ovarian follicle and subsequently aspirating the oocyte 105 by allowing for a second test tube or a third test tube of flushing fluid to be searched through. The contents of the ovarian follicle thus aspirated excluding the oocyte 105, followed by the flushing fluid and bodily fluids such as blood constitute the extraneous fluids. The extraneous fluids and the aspirated oocyte 105 together form the fluid mixture. The fluid mixture passes along the aspiration line 503 into the inlet tube 104 and then to the inlet channel 103 of the chamber 101 and reaches the receiving section 112 bounded by the closed lower end 102b of the hollow elongate tube 102 and the lower end 101b of the chamber 101, via the opening 103a at the lower end 101b of the chamber 101.

In an embodiment, the receiving section 112 of the hollow elongate tube 102 is then flushed with additional clean flushing fluid injected through the flushing line 505 by the syringe 504 until the hollow elongate tube 102 runs clear, to reduce the risk of clotting within the hollow elongate tube 102 and to allow macroscopic visualization of cumulus complexes. The aspiration needle 502 is, for example, a double lumen needle that enables the introduction of the flushing fluid from the syringe 504 and aspiration of the flushing fluid back up the aspiration line 503 at the same time. The flushing fluid is transferred directly from the syringe 504 to the end 502a of the aspiration needle 502 and then back up into the aspiration line 503 and then into the chamber 101. In another example, the aspiration assembly 501 uses a single lumen aspiration needle 502 that allows a follicle to be refilled and emptied in order to introduce clean flushing fluid into the chamber 101 of the oocyte separation apparatus 100.

The oocyte separation and collection system 500 may be configured to employ different variants of the aspiration assembly 501 based on a particular medical need. For example, if a follicle is bleeding, the aspiration assembly 501 may use a valve 509 to pass flushing fluid directly into the aspiration line 503. In an embodiment, as exemplarily illustrated in FIG. 5, the aspiration assembly 501 comprises the valve 509 or a tap that joins the aspiration line 503 to the flushing line 505. The connection between the aspiration line 503 and the flushing line 505 via the valve 509 allows a medical practitioner to divert the flushing fluid directly from the flushing line 505 to the aspiration line 503 bypassing the aspiration needle 502, thereby flushing the contents of the hollow elongate tube 102 until the fluid mixture runs clear. The valve 509 is positioned on the flushing line 505; therefore, the valve 509 switches between allowing the passage of the flushing fluid down along the aspiration needle 502 and allowing the passage of the flushing fluid directly into the aspiration line 503. A medical practitioner may open or close the valve 509 that connects the aspiration line 503 and the flushing line 505 to allow the flushing fluid to pass directly from the flushing line 505 to the aspiration line 503 and disallow passage of the flushing fluid back from the aspiration line 503 to the flushing line 505.

The outlet channel 110 of the oocyte separation apparatus 100 allows the passage of a substantial portion of the extraneous fluids out of the chamber 101 via the outlet tube 111 on application of a vacuum suction force by the vacuum suction element 507. In this example, the vacuum suction element 507 is a vacuum pump. The vacuum suction element 507 applies a vacuum suction force at the upper end 101a of the chamber 101 that draws out the substantial portion of the extraneous fluids from the outlet channel 110 through the vacuum suction line 506 into the waste collection container 508. The waste collection container 508 stores the extraneous fluids withdrawn from the oocyte separation apparatus 100 for further medical waste disposal procedures.

In an embodiment, the chamber 101 along with the stopper 108 and the aspiration assembly 501 may be removed from a first hollow elongate tube 102 and fitted into a second hollow elongate tube in order to aspirate additional follicles from the ovary. Therefore, the chamber 101 is reusable across multiple hollow elongate tubes. In an example, the first hollow elongate tube 102 is labeled and capped and placed into an appropriate culture system. The action of removing the chamber 101 from the hollow elongate tube 102 releases a vacuum and allows a substantial portion of the extraneous fluids trapped between the porous filter 107 and the opening 106c of the ceiling 106b of the separation unit 106 to flow back down into the receiving section 112 of the hollow elongate tube 102, thereby releasing oocytes 105 that may have adhered to the porous filter 107. The receiving section 112 in the hollow elongate tube 102 allows macroscopic visualization of a cumulus-oocyte complex within the hollow elongate tube 102. The presence of oocytes 105 in the receiving section 112 of the hollow elongate tube 102 may be confirmed by a microscopic visualization performed by a suitably experienced technician. If the oocyte 105 is not found in the original aspirate from the follicle, the medical practitioner typically flushes the follicle and proceeds to the next follicle.

Most medical practitioners do not like to wait to be told if the oocyte 105 has been found and therefore flush the follicle a couple of times and then proceed to the next follicle. This delays the process of analysis of the oocytes 105 for initiation of culturing by an embryologist since there is more fluid to search through to find the oocytes 105, that in turn adds to the total time duration of the complete procedure comprising aspiration of the contents of the follicle containing the oocytes 105, separation of the oocytes 105 from the other contents of the follicle, and analysis and culturing of the collected oocytes 105. Since the use of the oocyte separation apparatus 100 allows the removal of only the extraneous fluids from the fluid mixture transferred to the receiving section 112, the oocyte separation apparatus 100 disclosed herein therefore overcomes the risk of inadvertently discarding the oocytes 105 due to human error and considerably speeds up the complete procedure. Furthermore, since an oocyte/granulosa cell complex is visible to the naked eye, the oocytes 105 are fairly visible in a minimal volume of extraneous fluids retained in the receiving section 112 using the oocyte separation apparatus 100. Therefore, the oocyte separation apparatus 100 disclosed herein allows the presence of the oocyte/granulosa cell complex to be confirmed when the oocyte collection procedure is ongoing, thereby allowing the oocyte/granulosa cell complex to be collected for further culturing.

Figure 6:
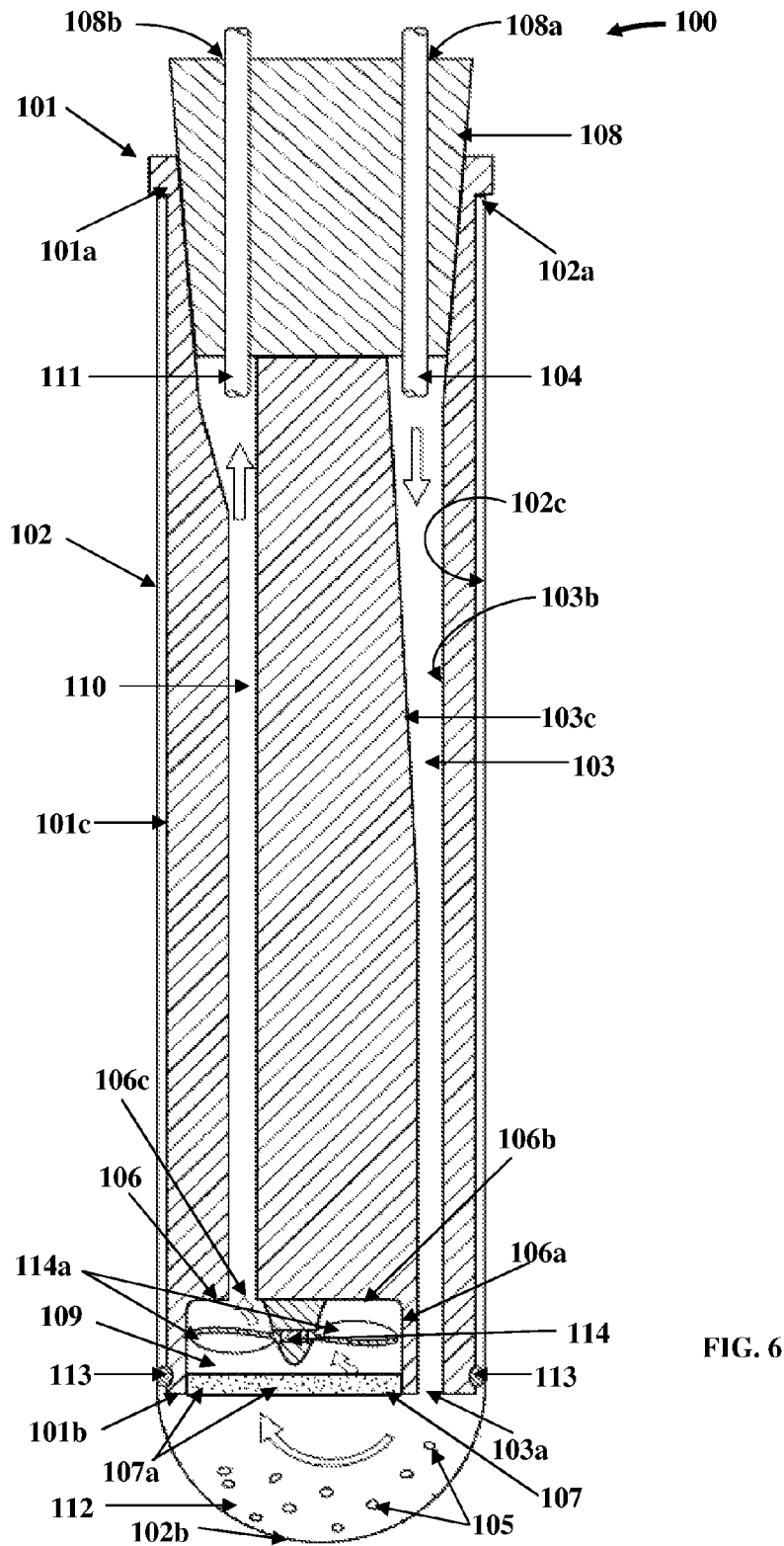
FIG. 6 exemplarily illustrates a sectional view of the oocyte separation apparatus inserted into the hollow elongate tube for separating and collecting one or more oocytes from a fluid mixture.

FIG. 6 exemplarily illustrates a sectional view of the oocyte separation apparatus 100 inserted into the hollow elongate tube 102 for separating and collecting one or more oocytes 105 from a fluid mixture. The oocyte separation apparatus 100 comprises the chamber 101, the inlet channel 103, the separation unit 106, and the outlet channel 110, as disclosed in the detailed description of FIGS. 1A-4. The dimensions of the chamber 101 are configured during the construction of the chamber 101, to provide for a close contact fit of the chamber 101 within the hollow elongate tube 102. Therefore, the chamber 101 is configured to fit into a hollow elongate tube 102, for example, a standard test tube snugly, based on the dimensions of the chamber 101 and the use of a mechanical gasket such as an O-ring seal. A stopper 108 is positioned in an air-tight and a water-tight configuration at the upper end 101a of the chamber 101. The stopper 108 is, for example, a silicone bung. The stopper 108 is, for example, a part of the aspiration assembly 501. The stopper 108 fits snugly into the chamber 101 and provides a passage for the inlet tube 104 and the outlet tube 111 to fit into the chamber 101 through the inlet channel 103 and the outlet channel 110 respectively. In an embodiment, the stopper 108 is flush mounted and sealed against the upper end 101a of the chamber 101.

The configuration of the inlet channel 103 for receiving the inlet tube 104 of the aspiration assembly 501 enables the inlet tube 104 to pass the fluid mixture directly to the closed lower end 102b of the hollow elongate tube 102. This reduces the impact of the drop of the fluid mixture to the closed lower end 102b of the hollow elongate tube 102 on the oocytes 105 from a point where the fluid mixture leaves the aspiration assembly 501 via the inlet tube 104 to a point where the oocytes 105 are collected at the closed lower end 102b of the hollow elongate tube 102. Furthermore, the configuration of the inlet channel 103 to receive the inlet tube 104 helps reduce the formation of air bubbles in the fluid mixture within the hollow elongate tube 102 due to the reduction in the amount of air within the chamber 101, and the reduction in the agitation of the fluid mixture caused by the drop of the fluid mixture to the closed lower end 102b of the hollow elongate tube 102. For example, in the absence of the oocyte separation apparatus 100, the fluid mixture may have a free fall drop of, for example, about 3 inches from where the fluid mixture enters the inlet tube 104 to the closed lower end 102b of the hollow elongate tube 102 where the fluid mixture is collected. Since the fluid mixture accelerates in free fall motion, the impact of the fluid mixture with the closed lower end 102b of the hollow elongate tube 102 may result in an undesirable damage to the oocytes 105. The oocyte separation apparatus 100 ensures maintenance of contact between the fluid mixture and the inner sides 103b and 103c of the inlet channel 103. The friction between the inner sides 103b and 103c of the inlet channel 103 and the fluid mixture mitigates the effect of gravity allowing the fluid mixture to flow down the inner sides 103b and 103c of the inlet channel 103 towards the closed lower end 102b of the hollow elongate tube 102. This reduces the possibility of formation of air bubbles at the closed lower end 102b of the hollow elongate tube 102 and reduces potential damage to the oocytes 105.

A vacuum suction element 507 operably coupled to the outlet tube 111 of the aspiration assembly 501 via a waste collection container 508 applies a vacuum suction force through the vacuum suction line 506 as exemplarily illustrated in FIG. 5. On application of the vacuum suction force by the vacuum suction element 507, the inlet channel 103, in fluid communication with the receiving section 112 bounded by the closed lower end 102b of the hollow elongate tube 102 and the lower end 101b of the chamber 101, via the opening 103a defined at the lower end 101b of the chamber 101, allows passage of the fluid mixture containing the oocytes 105 and the extraneous fluids from within the inlet channel 103 towards the closed lower end 102b of the hollow elongate tube 102. The receiving section 112 receives the fluid mixture from the inlet channel 103. The propeller 114 of the separation unit 106 is rotated by a flow of a substantial portion of the extraneous fluids into the space 109 in the separation unit 106 via the porous filter 107 on application of the vacuum suction force. The vacuum suction force applied by the vacuum suction element 507 via the vacuum suction line 506 aspirates the substantial portion of the extraneous fluids thereby assisting the rotation of the propeller 114. The propeller 114 is turned passively by the flow of the substantial portion of the extraneous fluids across the surface of one or more blades 114a of the propeller 114 towards the outlet channel 110. The propeller 114 agitates the substantial portion of the extraneous fluids for allowing unobstructed passage of the substantial portion of the extraneous fluids into the outlet channel 110 via the opening 106c in the ceiling 106b of the separation unit 106. Furthermore, the propeller 114 compactly collects fibrin elements from the extraneous fluids as they form as disclosed in the detailed description of FIG. 8.

The outlet channel 110 that is configured to receive the outlet tube 111 withdraws the substantial portion of the extraneous fluids separated from the fluid mixture out of the chamber 101 on application of the vacuum suction force, and allows the oocytes 105 to be retained and collected at the closed lower end 102b of the hollow elongate tube 102. The substantial portion of the extraneous fluids withdrawn by the outlet channel 110 via the outlet tube 111 is directed into the waste collection container 508 exemplarily illustrated in FIG. 5. The receiving section 112 retains and collects the oocytes 105 after the substantial portion of the extraneous fluids separated from the fluid mixture is withdrawn out of the chamber 101 via the outlet channel 110. Furthermore, the receiving section 112 retains a small volume of the fluid mixture comprising, for example, follicular fluid, the flushing fluid, and cellular matter including oocytes 105, with dimensions greater than or equal to the dimensions of the oocytes 105. This small volume of the fluid mixture can be contained, harvested for cell culture, or stored for analysis.

Figure 7:
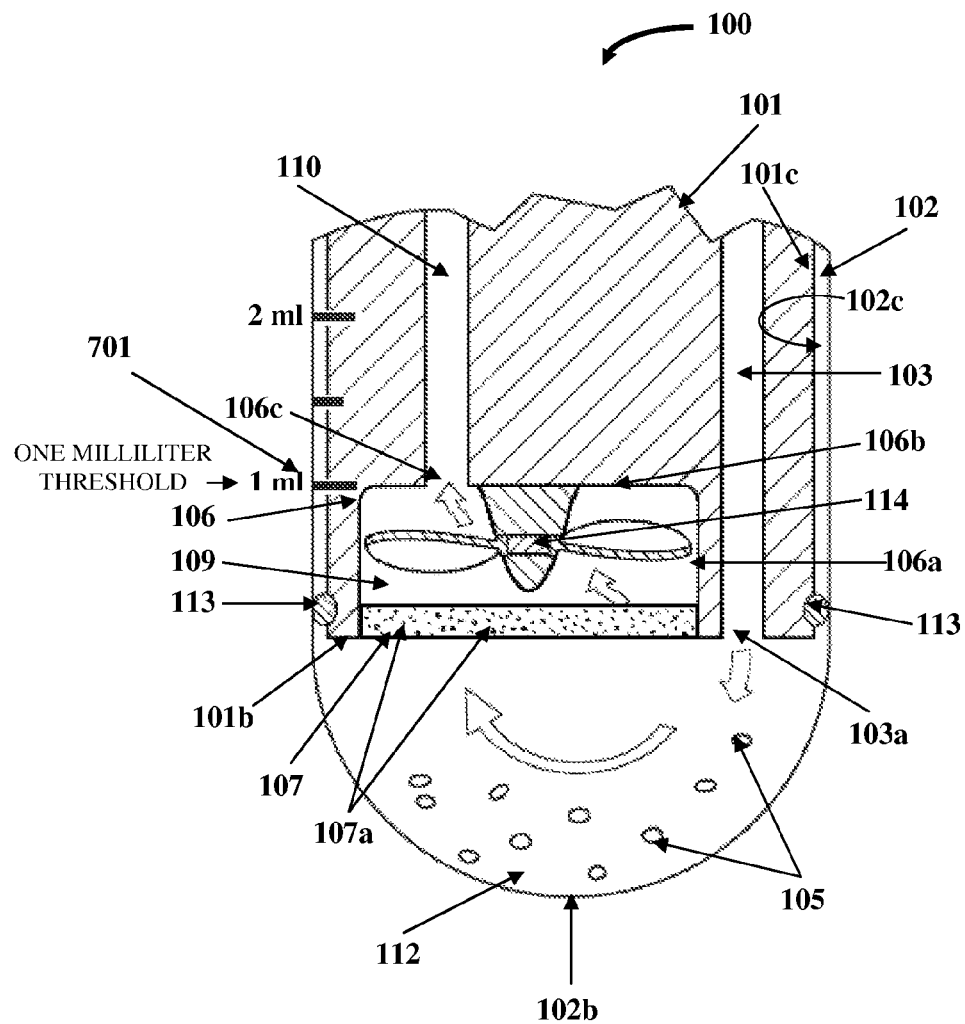
FIG. 7 exemplarily illustrates a partial sectional view of the oocyte separation apparatus inserted into the hollow elongate tube for separating and collecting one or more oocytes from a fluid mixture.

FIG. 7 exemplarily illustrates a partial sectional view of the oocyte separation apparatus 100 inserted into the hollow elongate tube 102 for separating and collecting one or more oocytes 105 from a fluid mixture. The bottom section of the oocyte separation apparatus 100 showing the inlet channel 103, the outlet channel 110, and the separation unit 106, and the receiving section 112 of the hollow elongate tube 102 are disclosed in the detailed description of FIGS. 1A-4. Furthermore, the hollow elongate tube 102, for example, a test tube is marked in intervals of one milliliter (ml). As exemplarily illustrated in FIG. 7, the separation unit 106 extends from the lower end 101b of the chamber 101 to the 1 milliliter threshold 701 marked on the hollow elongate tube 102. The separation unit 106 is positioned within the chamber 101 such that the separation unit 106 is disposed at a predetermined minimum volume marking on the hollow elongate tube 102, for example, corresponding to a one milliliter threshold 701 marked on the hollow elongate tube 102. Furthermore, a minimum volume of extraneous fluids, for example, one milliliter of extraneous fluids may be retained at the closed lower end 102b of the hollow elongate tube 102 with the oocytes 105. The hollow elongate tube 102 is capped as soon as the hollow elongate tube 102 is disconnected from the oocyte separation apparatus 100 to prevent evaporation of the retained extraneous fluids.

Figure 8:
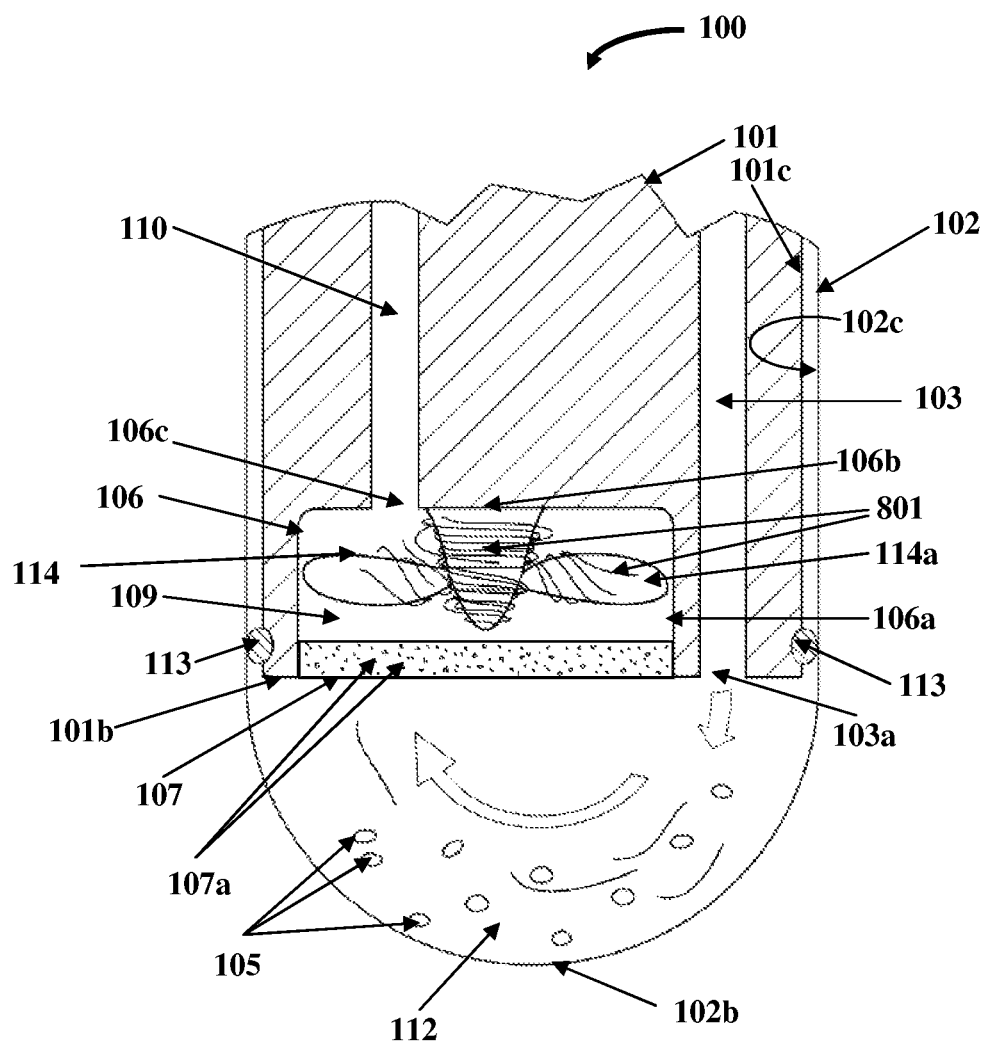
FIG. 8 exemplarily illustrates a partial sectional view of the oocyte separation apparatus, showing collection and compaction of fibrin elements on a propeller during rotation of the propeller.

FIG. 8 exemplarily illustrates a partial sectional view of the oocyte separation apparatus 100, showing collection and compaction of fibrin elements 801 on a propeller 114 during rotation of the propeller 114. The fibrin elements 801 that are a part of a substantial portion of the extraneous fluids of the fluid mixture and which are responsible for the clotting of blood cells may start to form as part of the clotting mechanism of blood, thereby leading to blood clots. Since the dimensions of the fibrin elements 801, for example, the fibrin threads or strands allow the fibrin elements 801 to pass through the pores 107a of the porous filter 107 on application of the vacuum suction force, the fibrin elements 801 may aggregate in the vicinity of the opening 106c of the ceiling 106b of the separation unit 106. The aggregated fibrin elements 801 in the vicinity of the opening 106c of the ceiling 106b of the separation unit 106 trigger the formation of blood clots that block the passage of the substantial portion of the extraneous fluids into the outlet channel 110. In order to inhibit the clotting of blood within the separation unit 106 and prevent a consequent blockage of the outlet channel 110, the propeller 114 collects and compacts the fibrin elements 801 on and around the blades 114a of the propeller 114 as they form during rotation of the propeller 114. The propeller 114 is rotated by the flow of the substantial portion of the extraneous fluids across the blades 114a on application of the vacuum suction force. The fibrin elements 801 which begin to form as part of the blood clotting process are collected and compacted on the blades 114a of the propeller 114 which impedes large clot formation within the separation unit 106.

Figure 9:
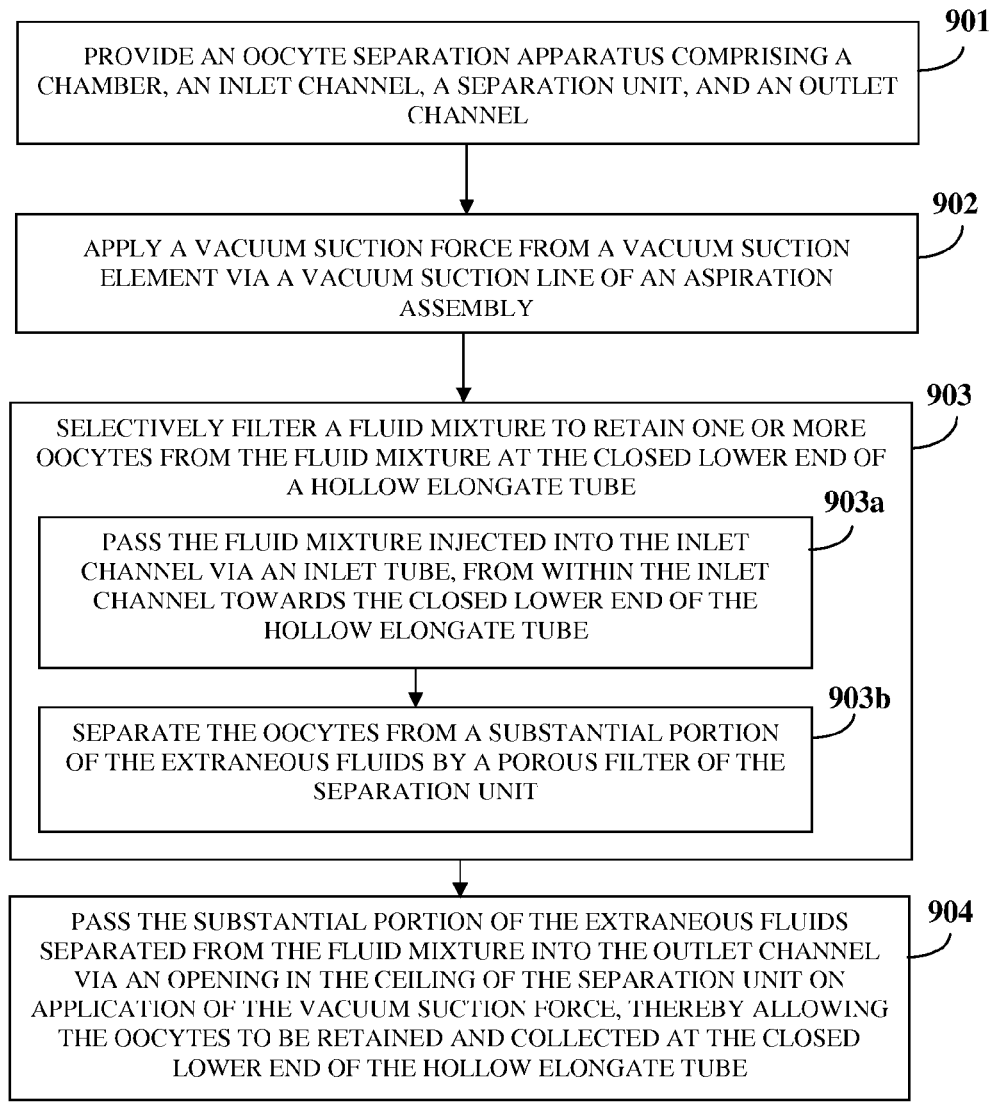
FIG. 9 illustrates a method for separating and collecting one or more oocytes from a fluid mixture.

FIG. 9 illustrates a method for separating and collecting one or more oocytes 105 from a fluid mixture. The method disclosed herein provides 901 the oocyte separation apparatus 100 comprising a chamber 101, an inlet channel 103, a separation unit 106, and an outlet channel 110 as exemplarily illustrated and disclosed in the detailed description of FIG. 1A. A vacuum suction element 507 operably coupled to the outlet tube 111 applies 902 a vacuum suction force via a vacuum suction line 506 of the aspiration assembly 501 exemplarily illustrated in FIG. 5. On application of the vacuum suction force from the vacuum suction element 507, the fluid mixture comprising one or more oocytes 105 and extraneous fluids is selectively filtered 903 to retain the oocytes 105 from the fluid mixture at the closed lower end 102b of the hollow elongate tube 102 as follows: The fluid mixture injected into the inlet channel 103 via the inlet tube 104 is passed 903a from within the inlet channel 103 towards the closed lower end 102b of the hollow elongate tube 102. The fluid mixture maintains contact with the inner sides 103b and 103c of the inlet channel 103 during passage of the fluid mixture through the inlet channel 103. The diameter of each of the pores 107a of the porous filter 107 is lesser than the diameter of each of the oocytes 105 and is configured to allow flow of a substantial portion of the extraneous fluids through the pores 107a of the porous filter 107 of the separation unit 106. The porous filter 107 therefore separates 903b the oocytes 105 from the substantial portion of the extraneous fluids and allows passage 904 of the substantial portion of the extraneous fluids separated from the fluid mixture into the outlet channel 110 via the opening 106c in the ceiling 106b of the separation unit 106, allowing the oocytes 105 to be retained and collected at the closed lower end 102b of the hollow elongate tube 102.

Figure 10:
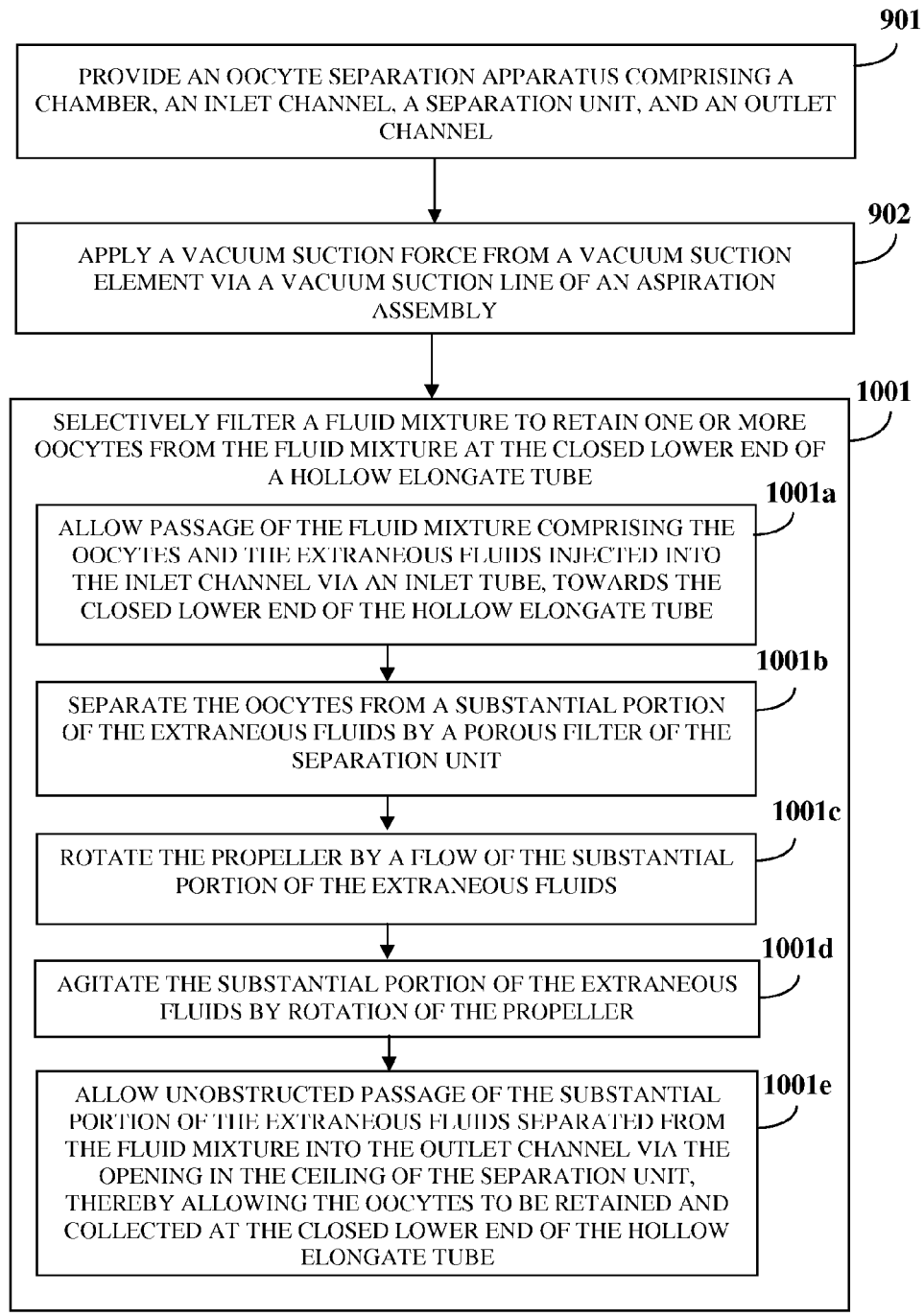
FIG. 10 illustrates an embodiment of the method for separating and collecting one or more oocytes from a fluid mixture.

FIG. 10 exemplarily illustrates an embodiment of the method for separating and collecting one or more oocytes 105 from a fluid mixture. The method disclosed herein provides 901 the oocyte separation apparatus 100 comprising a chamber 101, an inlet channel 103, a separation unit 106, and an outlet channel 110 as exemplarily illustrated and disclosed in the detailed description of FIG. 1B. The method disclosed herein performs the step 902 as disclosed in the detailed description of FIG. 9. The separation unit 106 of the oocyte separation apparatus 100 selectively filters 1001 the fluid mixture to retain one or more oocytes 105 from the fluid mixture at the closed lower end 102b of the hollow elongate tube 102 on application of the vacuum suction force from the vacuum suction element 507 of the aspiration assembly 501, where the vacuum suction element 507 is operably coupled to the outlet tube 111. In order to selectively filter the fluid mixture, the oocyte separation apparatus 100 allows 1001a passage of the fluid mixture comprising the oocytes 105 and the extraneous fluids injected into the inlet channel 103 via the inlet tube 104, from within the inlet channel 103 towards the closed lower end 102b of the hollow elongate tube 102. The fluid mixture maintains contact with the inner sides 103b and 103c of the inlet channel 103 during passage of the fluid mixture through the inlet channel 103. The porous filter 107 of the separation unit 106 separates 1001b the oocytes 105 from a substantial portion of the extraneous fluids.

The flow of a substantial portion of the extraneous fluids into the space 109 defined in the separation unit 106, via the porous filter 107 rotates 1001c the propeller 114 on application of the vacuum suction force. The rotation of the propeller 114 agitates 1001d a substantial portion of the extraneous fluids and allows 1001e unobstructed passage of the substantial portion of the extraneous fluids separated from the fluid mixture into the outlet channel 110 via the opening 106c in the ceiling 106b of the separation unit 106, allowing the oocytes 105 to be retained and collected at the closed lower end 102b of the hollow elongate tube 102. Furthermore, the rotation of the propeller 114 enables compact collection of fibrin elements 801 from the extraneous fluids on the propeller 114 as exemplarily illustrated in FIG. 8, to preclude clotting and allow unobstructed passage of the substantial portion of extraneous fluids into the outlet channel 110.

By avoiding a transfer of the fluid mixture containing the oocytes 105 to and from a Petri dish which may damage the oocytes 105 due to variations in the temperature of the Petri dish, changes in potential hydrogen (pH) levels, osmolarity, etc., at different stages in the process of oocyte separation and collection, the oocyte separation apparatus 100 disclosed herein protects and maintains the temperature, pH level, osmolarity, etc., of the oocytes 105 within the aspiration assembly 501 and the chamber 101. The oocyte separation apparatus 100 disclosed herein thereby precludes or reduces exposure of the oocytes 105 to temperature variations that may expose the oocytes 105 to thermal stress which may interfere with the viability of maintaining the oocytes 105 in a culturing system.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention in its aspects.

I claim:

1. An apparatus for separating and collecting one or more oocytes from a fluid mixture, comprising:
    a chamber configured for insertion into a hollow elongate tube, said hollow elongate tube having an open upper end and a closed lower end, said chamber comprising an upper end and a lower end;
    an inlet channel extending within said chamber from said upper end of said chamber to said lower end of said chamber, wherein said inlet channel is configured to receive an inlet tube of an aspiration assembly that injects said fluid mixture comprising said one or more oocytes and extraneous fluids into said inlet channel towards said closed lower end of said hollow elongate tube;
    a separation unit positioned within said chamber at said lower end of said chamber, said separation unit comprising one or more walls and a ceiling, said separation unit further comprising a porous filter rigidly positioned within a cavity defined at said lower end of said chamber, wherein said porous filter is configured to selectively filter said fluid mixture to retain said one or more oocytes from said fluid mixture at said closed lower end of said hollow elongate tube; and an outlet channel extending longitudinally from an opening in said ceiling of said separation unit to said upper end of said chamber, wherein said outlet channel is configured to receive an outlet tube of said aspiration assembly for allowing a substantial portion of said extraneous fluids separated from said fluid mixture to be withdrawn out of said chamber on an application of a vacuum suction force, and for allowing said one or more oocytes to be retained and collected at said closed lower end of said hollow elongate tube.

2. The apparatus of claim 1, wherein said separation unit further comprises a propeller rigidly suspended from said ceiling of said separation unit within a space defined by said porous filter, said one or more walls, and said ceiling of said separation unit, wherein said propeller is rotated by a flow of said substantial portion of said extraneous fluids into said defined space via said porous filter on said application of said vacuum suction force, thereby agitating said substantial portion of said extraneous fluids for allowing unobstructed passage of said substantial portion of said extraneous fluids into said outlet channel via said opening in said ceiling of said separation unit.

3. The apparatus of claim 2, wherein said rotation of said propeller enables compact collection of fibrin elements from said extraneous fluids on said propeller to preclude clotting for said unobstructed passage of said substantial portion of said extraneous fluids into said outlet channel.

4. An apparatus for separating and collecting one or more oocytes from a fluid mixture, comprising:
a chamber configured for insertion into a hollow elongate tube, said hollow elongate tube having an open upper end and a closed lower end, said chamber comprising an upper end and a lower end;
an inlet channel extending within said chamber from said upper end of said chamber to said lower end of said chamber, wherein said inlet channel is configured to receive an inlet tube of an aspiration assembly that injects said fluid mixture comprising said one or more oocytes and extraneous fluids into said inlet channel towards said closed lower end of said hollow elongate tube, said fluid mixture maintaining contact with inner sides of said inlet channel during passage of said fluid mixture through said inlet channel;
a separation unit positioned within said chamber at said lower end of said chamber, said separation unit comprising one or more walls and a ceiling, said separation unit further comprising:
a porous filter rigidly positioned within a cavity defined at said lower end of said chamber, wherein said porous filter is configured to selectively filter said fluid mixture to retain said one or more oocytes from said fluid mixture at said closed lower end of said hollow elongate tube; and
a propeller rigidly suspended from said ceiling of said separation unit within a space defined by said porous filter, said one or more walls, and said ceiling of said separation unit, wherein said propeller is rotated by a flow of a substantial portion of said extraneous fluids into said defined space via said porous filter on an application of a vacuum suction force, thereby agitating said substantial portion of said extraneous fluids for allowing unobstructed passage of said substantial portion of said extraneous fluids into an outlet channel via an opening in said ceiling of said separation unit; and said outlet channel extending longitudinally from said opening in said ceiling of said separation unit to said upper end of said chamber, wherein said outlet channel is configured to receive an outlet tube of said aspiration assembly for allowing said substantial portion of said extraneous fluids separated from said fluid mixture to be withdrawn out of said chamber on said application of said vacuum suction force, and for allowing said one or more oocytes to be retained and collected at said closed lower end of said hollow elongate tube.

5. The apparatus of claim 4, wherein said rotation of said propeller enables compact collection of fibrin elements from said extraneous fluids on said propeller to preclude clotting for said unobstructed passage of said substantial portion of said extraneous fluids into said outlet channel.

6. The apparatus of claim 4, wherein said chamber is in gripping contact with an inner wall surface of said hollow elongate tube.

7. The apparatus of claim 6, further comprising a sealing element configured to provide said gripping contact between said chamber and said inner wall surface of said hollow elongate tube.

8. The apparatus of claim 4, wherein said inlet channel is in fluid communication with a receiving section bounded by said closed lower end of said hollow elongate tube and said lower end of said chamber, via an opening defined at said lower end of said chamber for allowing passage of said fluid mixture from within said inlet channel towards said closed lower end of said hollow elongate tube.

9. The apparatus of claim 8, wherein said receiving section receives said fluid mixture from said inlet channel and retains and collects said one or more oocytes after said substantial portion of said extraneous fluids separated from said fluid mixture is withdrawn out of said chamber via said outlet channel.

10. The apparatus of claim 4, wherein said outlet channel is in fluid communication with said space defined by said porous filter, said one or more walls, and said ceiling of said separation unit via said opening in said ceiling for allowing passage of said substantial portion of said extraneous fluids separated from said fluid mixture out of said chamber.

11. The apparatus of claim 4, wherein said inlet channel receives said inlet tube via a first longitudinal opening of a stopper positioned in a fluid tight configuration at said upper end of said chamber, for receiving said fluid mixture from said aspiration assembly via said inlet tube.

12. The apparatus of claim 4, wherein said outlet channel receives said outlet tube via a second longitudinal opening of a stopper positioned in a fluid tight configuration at said upper end of said chamber for allowing said substantial portion of said extraneous fluids to be withdrawn from said space defined by said porous filter, said one or more walls, and said ceiling of said separation unit.

13. The apparatus of claim 4, wherein said outlet channel allows said substantial portion of said extraneous fluids to be withdrawn from said space defined by said porous filter, said one or more walls, and said ceiling of said separation unit via said outlet tube on said application of said vacuum suction force from a vacuum suction element of said aspiration assembly operably coupled to said outlet tube.

14. The apparatus of claim 4, wherein said porous filter comprises a plurality of pores for said selective filtering of said fluid mixture to retain said one or more oocytes at said closed lower end of said hollow elongate tube, wherein a diameter of each of said pores of said porous filter is lesser than a diameter of each of said one or more oocytes and is configured to allow said flow of said substantial portion of said extraneous fluids through said pores of said porous filter.

15. A method for separating and collecting one or more oocytes from a fluid mixture, comprising:
providing an oocyte separation apparatus comprising:
a chamber configured for insertion into a hollow elongate tube, said hollow elongate tube having an open upper end and a closed lower end, said chamber comprising an upper end and a lower end;
an inlet channel extending within said chamber from said upper end of said chamber to said lower end of said chamber, wherein said inlet channel is configured to receive an inlet tube of an aspiration assembly that injects said fluid mixture comprising said one or more oocytes and extraneous fluids into said inlet channel towards said closed lower end of said hollow elongate tube;
a separation unit positioned within said chamber at said lower end of said chamber, said separation unit comprising one or more walls and a ceiling, said separation unit further comprising a porous filter rigidly positioned within a cavity defined at said lower end of said chamber; and
an outlet channel extending longitudinally from an opening in said ceiling of said separation unit to said upper end of said chamber, wherein said outlet channel is configured to receive an outlet tube of said aspiration assembly that allows a substantial portion of said extraneous fluids separated from said fluid mixture to be withdrawn out of said chamber on an application of a vacuum suction force;
selectively filtering said fluid mixture to retain said one or more oocytes from said fluid mixture at said closed lower end of said hollow elongate tube on said application of said vacuum suction force from a vacuum suction element of said aspiration assembly, said vacuum suction element being operably coupled to said outlet tube, wherein said selective filtering of said fluid mixture comprises:
allowing passage of said fluid mixture comprising said one or more oocytes and said extraneous fluids injected into said inlet channel via said inlet tube, from within said inlet channel towards said closed lower end of said hollow elongate tube, said fluid mixture maintaining contact with inner sides of said inlet channel during said passage of said fluid mixture through said inlet channel; and
separating said one or more oocytes from said substantial portion of said extraneous fluids by said porous filter of said separation unit; and
allowing passage of said substantial portion of said extraneous fluids separated from said fluid mixture into said outlet channel via said opening in said ceiling of said separation unit on said application of said vacuum suction force, thereby allowing said one or more oocytes to be retained and collected at said closed lower end of said hollow elongate tube.

16. The method of claim 15, wherein said inlet channel of said oocyte separation apparatus is in fluid communication with a receiving section bounded by said closed lower end of said hollow elongate tube and said lower end of said chamber, via an opening defined at said lower end of said chamber for allowing said passage of said fluid mixture from within said inlet channel towards said closed lower end of said hollow elongate tube, wherein said receiving section receives said fluid mixture from said inlet channel and retains and collects said one or more oocytes after said substantial portion of said extraneous fluids separated from said fluid mixture is withdrawn out of said chamber via said outlet channel.

17. The method of claim 15, wherein said outlet channel of said oocyte separation apparatus is in fluid communication with a space defined by said porous filter, said one or more walls, and said ceiling of said separation unit via said opening in said ceiling for allowing said passage of said substantial portion of said extraneous fluids separated from said fluid mixture out of said chamber.

18. A method for separating and collecting one or more oocytes from a fluid mixture, comprising:
providing an oocyte separation apparatus comprising:
a chamber configured for insertion into a hollow elongate tube, said hollow elongate tube having an open upper end and a closed lower end, said chamber comprising an upper end and a lower end;
an inlet channel extending within said chamber from said upper end of said chamber to said lower end of said chamber, wherein said inlet channel is configured to receive an inlet tube of an aspiration assembly that injects said fluid mixture comprising said one or more oocytes and extraneous fluids into said inlet channel towards said closed lower end of said hollow elongate tube;
a separation unit positioned within said chamber at said lower end of said chamber, said separation unit comprising one or more walls and a ceiling, said separation unit further comprising:
a porous filter rigidly positioned within a cavity defined at said lower end of said chamber; and
a propeller rigidly suspended from said ceiling of said separation unit within a space defined by said porous filter, said one or more walls, and said ceiling of said separation unit; and
an outlet channel extending longitudinally from an opening in said ceiling of said separation unit to said upper end of said chamber, wherein said outlet channel is configured to receive an outlet tube of said aspiration assembly that allows a substantial portion of said extraneous fluids separated from said fluid mixture to be withdrawn out of said chamber on an application of a vacuum suction force;
selectively filtering said fluid mixture to retain said one or more oocytes from said fluid mixture at said closed lower end of said hollow elongate tube on said application of said vacuum suction force from a vacuum suction element of said aspiration assembly, said vacuum suction element being operably coupled to said outlet tube, wherein said selective filtering of said fluid mixture comprises:
allowing passage of said fluid mixture comprising said one or more oocytes and said extraneous fluids injected into said inlet channel via said inlet tube, from within said inlet channel towards said closed lower end of said hollow elongate tube, said fluid mixture maintaining contact with inner sides of said inlet channel during said passage of said fluid mixture through said inlet channel; and
separating said one or more oocytes from said substantial portion of said extraneous fluids by said porous filter of said separation unit; and
allowing unobstructed passage of said substantial portion of said extraneous fluids separated from said fluid mixture into said outlet channel via said opening in said ceiling of said separation unit on said application of said vacuum suction force, by agitating said substantial portion of said extraneous fluids by rotation of said propeller of said separation unit, thereby allowing said one or more oocytes to be retained and collected at said closed lower end of said hollow elongate tube.

19. The method of claim 18, wherein said rotation of said propeller is performed by a flow of said substantial portion of said extraneous fluids into said space in said separation unit via said porous filter, on said application of said vacuum suction force.

20. The method of claim 18, further comprising compactly collecting fibrin elements from said extraneous fluids on said propeller to preclude clotting for said unobstructed passage of said substantial portion of said extraneous fluids into said outlet channel.

21. The method of claim 18, wherein said inlet channel of said oocyte separation apparatus is in fluid communication with a receiving section bounded by said closed lower end of said hollow elongate tube and said lower end of said chamber, via an opening defined at said lower end of said chamber for allowing said passage of said fluid mixture from within said inlet channel towards said closed lower end of said hollow elongate tube.

22. The method of claim 21, wherein said receiving section receives said fluid mixture from said inlet channel and retains and collects said one or more oocytes after said substantial portion of said extraneous fluids separated from said fluid mixture is withdrawn out of said chamber via said outlet channel.

23. The method of claim 18, wherein said outlet channel of said oocyte separation apparatus is in fluid communication with said space defined by said porous filter, said one or more walls, and said ceiling of said separation unit via said opening in said ceiling for allowing said unobstructed passage of said substantial portion of said extraneous fluids separated from said fluid mixture out of said chamber.

24. The method of claim 18, wherein said inlet channel of said oocyte separation apparatus receives said inlet tube via a first longitudinal opening of a stopper positioned in a fluid tight configuration at said upper end of said chamber, for receiving said fluid mixture from said aspiration assembly via said inlet tube.

25. The method of claim 18, wherein said outlet channel of said oocyte separation apparatus receives said outlet tube via a second longitudinal opening of a stopper positioned in a fluid tight configuration at said upper end of said chamber for allowing said substantial portion of said extraneous fluids to be withdrawn from said space defined by said porous filter, said one or more walls, and said ceiling of said separation unit.

26. The method of claim 18, wherein said outlet channel of said oocyte separation apparatus allows said substantial portion of said extraneous fluids to be withdrawn from said space defined by said porous filter, said one or more walls, and said ceiling of said separation unit via said outlet tube on said application of said vacuum suction force from said vacuum suction element.

* * * * *